US011406563B2

(12) United States Patent
Bennett et al.

(10) Patent No.: US 11,406,563 B2
(45) Date of Patent: Aug. 9, 2022

(54) ORAL IMMUNOTHERAPY UNIT DOSE DISPENSING SYSTEMS AND METHODS

(71) Applicant: Société des Produits Nestlé S.A., Vevey (CH)

(72) Inventors: Kristin Bennett, Larkspur, CA (US); Michael S. Holfinger, Mountain View, CA (US); Naomi Korn Gold, Sharon, MA (US); Christine Horan, Northborough, MA (US); Michel Arney, Sudbury, MA (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 222 days.

(21) Appl. No.: 16/523,875

(22) Filed: Jul. 26, 2019

(65) Prior Publication Data
US 2020/0030187 A1    Jan. 30, 2020

Related U.S. Application Data

(60) Provisional application No. 62/711,336, filed on Jul. 27, 2018.

(51) Int. Cl.
*A61J 1/03* (2006.01)
*A61J 7/00* (2006.01)
(Continued)

(52) U.S. Cl.
CPC ............. *A61J 1/035* (2013.01); *A61J 7/0069* (2013.01); *A61J 7/0076* (2013.01); *A61J 7/0092* (2013.01);
(Continued)

(58) Field of Classification Search
CPC ........ A61J 1/035; A61J 7/0069; A61J 7/0076; A61J 7/0092; A61J 7/04; A61K 9/14; A61F 17/00
(Continued)

(56) References Cited

U.S. PATENT DOCUMENTS 3,931,885 A * 1/1976 Nahill .................... B65D 75/30
206/538
4,889,238 A * 12/1989 Batchelor ............ B65D 43/169
206/535

(Continued)

FOREIGN PATENT DOCUMENTS

WO   WO2005109948 A2   11/2005
WO   WO2005109948 A3    4/2006
(Continued)

OTHER PUBLICATIONS

Guidance for Industry (Apr. 1, 2013). "Safety Considerations for Container Labels and Carton Labeling Design to Minimize Medication Errors," 26 pages.
(Continued)

*Primary Examiner* — Steven A. Reynolds
(74) *Attorney, Agent, or Firm* — Morrison Foerster LLP

(57) ABSTRACT

Systems and containers for organizing and administering an oral immunotherapy regimen to a patient are disclosed herein. One aspect of the present technology is directed systems for efficiently and safely identifying pre-packaged dose units to administer to a patient undergoing oral immunotherapy. Further aspects of the present technology are directed to reducing medical staff dosing errors when administering an oral immunotherapy regimen. In one embodiment, the system includes a plurality of dosage containers, wherein each dosage container includes dosage identification characteristics corresponding to dosage of an oral immunotherapy composition. Further aspects of the present technology are directed to methods of dispensing an oral immunotherapy composition to a patient in a manner that mitigates the risk of errors in oral immunotherapy dose administration.

29 Claims, 11 Drawing Sheets

(51) Int. Cl.
*G16H 20/10* (2018.01)
*A61J 7/04* (2006.01)
*A61K 9/14* (2006.01)

(52) U.S. Cl.
CPC .................. *A61J 7/04* (2013.01); *A61K 9/14* (2013.01); *G16H 20/10* (2018.01)

(58) Field of Classification Search
USPC .......................................... 206/528, 531, 538
See application file for complete search history.

(56) References Cited

U.S. PATENT DOCUMENTS

| | | | |
|---|---|---|---|
| 6,375,956 B1 | 4/2002 | Hermelin | |
| 7,451,876 B2 * | 11/2008 | Bossi | A61J 1/035 206/459.5 |
| 7,715,277 B2 | 5/2010 | De La Huerga | |
| 8,266,878 B2 | 9/2012 | Luciano, Jr. et al. | |
| 9,198,869 B2 | 12/2015 | Walser | |
| 9,314,401 B2 | 4/2016 | Taurel | |
| 9,481,716 B2 | 11/2016 | Clark | |
| 9,492,535 B2 | 11/2016 | Walser | |
| 10,086,068 B2 | 10/2018 | Walser | |
| 10,358,247 B2 * | 7/2019 | Chudy | B65B 5/103 |
| 10,449,118 B2 | 10/2019 | Walser | |
| D866,320 S | 11/2019 | Bennet et al. | |
| D866,321 S | 11/2019 | Bennet et al. | |
| D866,322 S | 11/2019 | Bennet et al. | |
| 10,512,686 B2 | 12/2019 | Walser et al. | |
| 2004/0148054 A1 | 7/2004 | Schwartz | |
| 2006/0278557 A1 | 12/2006 | Firestone | |
| 2008/0027291 A1 | 1/2008 | Williams-hartman | |
| 2009/0261014 A1 * | 10/2009 | Reape | A61K 31/519 206/531 |
| 2010/0071320 A1 | 3/2010 | Ali | |
| 2012/0037517 A1 * | 2/2012 | Grosskopf | A61J 1/035 206/1.5 |
| 2014/0093541 A1 | 4/2014 | Clark | |
| 2014/0271721 A1 * | 9/2014 | Walser | G01N 33/6893 424/275.1 |
| 2016/0051593 A1 | 2/2016 | Raff | |
| 2017/0021010 A1 | 1/2017 | Erstein | |
| 2017/0095619 A1 | 4/2017 | Baker | |
| 2017/0107038 A1 * | 4/2017 | Kim | B65D 77/22 |
| 2017/0367970 A1 | 12/2017 | Jacobi | |
| 2018/0042816 A1 | 2/2018 | Walser | |
| 2018/0200361 A1 | 7/2018 | Simon | |
| 2019/0167785 A1 | 6/2019 | Dilly | |
| 2019/0175723 A1 | 6/2019 | Walser | |
| 2019/0192652 A1 | 6/2019 | Walser | |
| 2019/0247444 A1 | 8/2019 | Raff | |

FOREIGN PATENT DOCUMENTS

| | | |
|---|---|---|
| WO | WO2014159607 A1 | 10/2014 |
| WO | WO2014159609 A1 | 10/2014 |
| WO | WO2015187736 A1 | 12/2015 |
| WO | WO2016033094 A1 | 3/2016 |
| WO | WO2016033094 A9 | 8/2016 |
| WO | WO2018132733 A1 | 7/2018 |
| WO | WO2019089978 A1 | 5/2019 |

OTHER PUBLICATIONS

International Preliminary Report on Patentability, dated Feb. 2, 2021, for PCT Application No. PCT/US2009/043767, filed Jul. 26, 2019, 8 pages.
International Search Report and Written Opinion, dated Dec. 2, 2019, for PCT Application No. PCT/US2009/043767, filed Jul. 26, 2019, 12 pages.
Butschli, J et al. (Apr. 10, 2014). "Noven Therapeutics Earns HCPC's 2013 Compliance Package of the Year," Healthcare Packaging, retrieved from https://www.healthcarepackaging.com/print/11903, last visited Oct. 3, 2019, 3 pages.
Design U.S. Appl. No. 29/658,124, Adelman, filed Aug. 15, 2019. (Copy not submitted herewith pursuant to waiver of 37 C.F.R. § 1.98(a)(2)(iii) issued by the Office on Sep. 21, 2004).
Design U.S. Appl. No. 29/658,129, Adelman, filed Aug. 15, 2019. (Copy not submitted herewith pursuant to waiver of 37 C.F.R. § 1.98(a)(2)(iii) issued by the Office on Sep. 21, 2004).
Design U.S. Appl. No. 29/658,130, Adelman, filed Aug. 15, 2019. (Copy not submitted herewith pursuant to waiver of 37 C.F.R. § 1.98(a)(2)(iii) issued by the Office on Sep. 21, 2004).
U.S. Appl. No. 16/453,871, Walser et al., filed Jun. 26, 2019 (Copy not submitted herewith pursuant to vaiverof 37 C.F.R. § 1 98(a)(2)(iii) issued by the Office on Sep. 21, 2004).
U.S. Appl. No. 16/542,198, Adelman, filed Aug. 15, 2019 (Copy not submitted herewith pursuant to vaiverof 37 C.F.R. § 1 98(a)(2)(iii) issued by the Office on Sep. 21, 2004).
Extended European Search Report, dated Apr. 4, 2022, for European Patent Application No. 19839815.8, 11 pages.

* cited by examiner

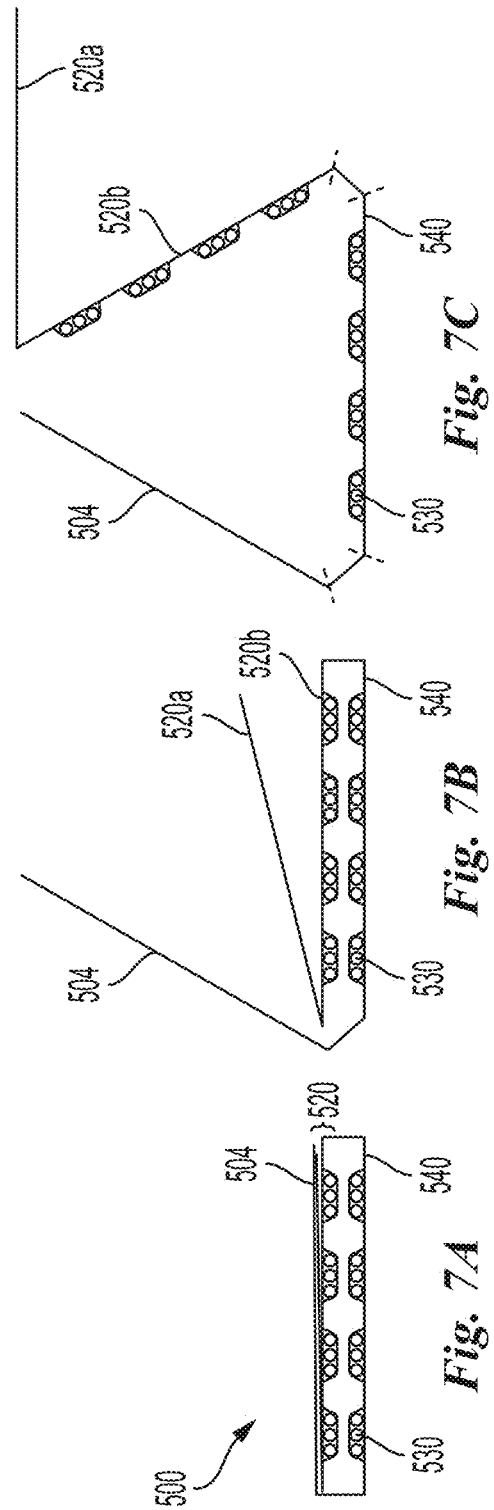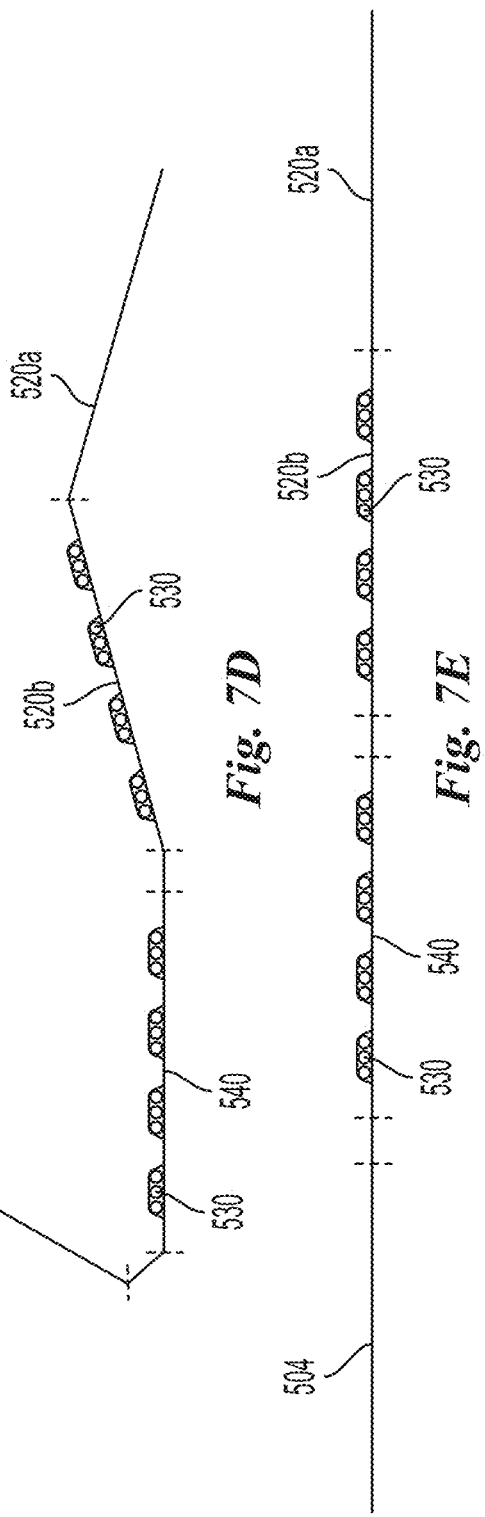

ORAL IMMUNOTHERAPY UNIT DOSE DISPENSING SYSTEMS AND METHODS

CROSS-REFERENCE TO RELATED APPLICATION

This application claims the benefit of U.S. Provisional Application No. 62/711,336, filed on Jul. 27, 2018; which is incorporated herein by reference in its entirety for all purposes.

TECHNICAL FIELD

The present invention relates to systems and system components for dispensing dose units for oral immunotherapy treatments, as well as associated methods of use.

BACKGROUND

Food allergies are caused, in most cases, by an immunological reaction to proteins in the food. In the early years of life, the immune system is still developing and may fail to develop tolerance to dietary antigens (this may also be described as insufficient induction of oral tolerance). The result is that the baby or child mounts an exaggerated immune response to the dietary protein and develops an allergic response to it. The most common food allergies in children are peanuts, tree nuts, milk and eggs. Specific immunotherapy for food allergy, including peanut allergy among others, in the forms of oral immunotherapy (OIT) and sublingual immunotherapy (SLIT) has been studied in recent years and has demonstrated encouraging safety and efficacy results in early clinical trials, including beneficial immunologic changes. OIT has shown evidence for inducing desensitization in most subjects with immunologic changes over time indicating progression toward clinical tolerance.

Compositions (e.g., formulations) comprising offending allergens (e.g., proteins, protein epitopes) can be prepared for administration in tailored regimens for OIT. Subjects treated with such compositions may exhibit, over time, a decreased anaphylactic reaction, a decreased humoral response and/or T cell response, a decreased IgE response and/or a decreased mast cell response associated with exposure to an offending allergen following treatment with an OIT regimen. In certain scenarios, a subject treated with such compositions in an OIT regimen may be desensitized to the offending allergen (e.g., peanuts, milk, egg, tree nuts, etc.) and may be better able to withstand an oral food challenge following treatment.

SUMMARY

According to some embodiments, a system for administering an oral immunotherapy regimen to a patient includes a plurality of dosage containers comprising a plurality of detached single dose packages comprising the same dosage of an oral immunotherapy composition, wherein the single dose packages in different dosage containers comprise different dosages of the oral immunotherapy composition, and wherein the dosage containers comprises a dosage identifier that associates the dosage container with the dosage of oral immunotherapy composition contained by the single dose packages contained in the dosage container; and a housing having an internal cavity that retains the plurality of dosage containers.

In any of these embodiments, the single dose packages may include the dosage identifier.

In any of these embodiments, the dosage identifier may be a dosage level of the oral immunotherapy composition.

In any of these embodiments, the dosage identifier may include color-coding or shade-coding, and wherein each dosage is associated with a different color or shading.

In any of these embodiments, the dosage identifier may include numeric coding, and wherein the numeric coding indicates an order in which the dosage levels increase or decrease.

In any of these embodiments, the dosage identifier may include the dosage.

In any of these embodiments, the oral immunotherapy composition may be a powder.

In any of these embodiments, the plurality of single dose packages may include one or more capsules or tablets comprising the oral immunotherapy composition.

In any of these embodiments, the one or more capsules or tablets may be visible without opening the single dose package.

In any of these embodiments, the one or more capsules or tablets may be arranged in a configuration associated with the dosage identifier for the dosage container.

In any of these embodiments, the system may further include a dosage configuration guide that associates the configuration to the dosage identifier.

In any of these embodiments, dosage containers may include a plurality of supports spaced apart along a length of an inner wall of the dosage container, and wherein the dosage containers are configured to hold a single dose package in a substantially vertical orientation between the supports.

In any of these embodiments, the system may further include an initial escalation module containing a plurality of initial escalation folios comprising a plurality of dose units in increasing dosage levels.

In any of these embodiments, the system may further include a maintenance dosage container containing a plurality of maintenance dose units having the same dosage of the oral immunotherapy composition.

In any of these embodiments, the dosage containers may be configured to be refilled with single dose packages.

In any of these embodiments, each dosage container may be configured to be individually removed from the housing and replaced with a new dosage container.

In any of these embodiments, the system may include 3, 4, 5, or 6 or more different dosage containers.

In any of these embodiments, the system may include between 3 and about 100 different dosage containers.

In any of these embodiments, the oral immunotherapy composition may include a peanut, tree nut, egg, dairy, or shellfish composition.

In any of these embodiments, the system may further include an initial escalation folio comprising a series of escalating dose units comprising the oral immunotherapy composition.

In any of these embodiments, the series of dose units may include at least one dose unit with a dosage of the oral immunotherapy composition that is lower than the lowest dosage of the single dose packages in any of the dosage containers.

In any of these embodiments, the escalating dose units may be arranged in different configurations to identify different dosages.

In any of these embodiments, the initial escalation folio may be contained within the housing.

In any of these embodiments, the housing may be configured to contain a plurality of initial escalation folios in a compartment of the housing.

In any of these embodiments, the system may further include a dosage folio that includes a dosage identifier that associates the dosage folio to a dosage container within the plurality of dosage containers, and a plurality of daily dose units comprising the oral immunotherapy composition associated with the dosage identifier.

In any of these embodiments, the dosage folio may include a patient log comprising a space identified for recording a date of administration of a daily dose unit.

In any of these embodiments, the dosage folio may include a patient log comprising a space identified for recording a reactive symptom following ingestion of the daily dose unit.

In any of these embodiments, the system may include a plurality of dosage folios comprising different dosage identifiers, wherein the dosage folios comprise a plurality of daily dose units that correspond with the dosage identifier of the dosage folio.

According to some embodiments, a dosage folio includes a plurality of daily dose units comprising an oral immunotherapy composition, wherein each daily dose unit is independently openable and comprises a plurality of capsules or tablets; and a dosage identifier associated with the dosage of the daily dose units.

In any of these embodiments, the dosage folio may include a patient log, wherein the patient log comprises a space identified for recording a date of administration of a daily dose unit.

In any of these embodiments, the patient log may include a space identified for recording a reactive symptoms following ingestion of the daily dose unit.

In any of these embodiments, the dosage folio may include pictorial instructions for administering the oral immunotherapy composition.

In any of these embodiments, the dosage identifier may be a dosage level of the oral immunotherapy composition.

In any of these embodiments, the dosage identifier may include a color code or a shade code.

In any of these embodiments, the dosage identifier may include a numeric code.

In any of these embodiments, the dosage identifier may include the dosage of the daily dose units.

In any of these embodiments, the oral immunotherapy composition may be a powder.

In any of these embodiments, the daily dose units may be arranged in a grid pattern and a grid pattern location associated with a first day lacks a daily dose unit.

In any of these embodiments, the capsules or tablets may be arranged in a configuration associated with the dosage identifier for the folio.

In any of these embodiments, the oral immunotherapy composition may include a peanut, tree nut, egg, dairy, or shellfish composition.

In any of these embodiments, the dosage folio may include about 7 to about 35 daily dose units.

According to some embodiments, a method of dispensing a selected dosage of an oral immunotherapy composition to a patient includes identifying a dosage container associated with a selected dosage of the oral immunotherapy composition using a dosage identifier on the dosage container, wherein the dosage container is identified from a plurality of different dosage containers comprising different dosage identifiers associated with different dosages of the oral immunotherapy composition; removing a single dose package comprising the selected amount of the oral immunotherapy composition from the identified dosage container; and dispensing the selected dosage of the oral immunotherapy composition to the patient.

According to some embodiments, a method of retrieving a single dose package comprising a selected dosage of an oral immunotherapy composition includes identifying a dosage container associated with the selected dosage of the oral immunotherapy composition using a dosage identifier on the dosage container, wherein the dosage container is identified from a plurality of different dosage containers comprising different dosage identifiers associated with different dosages of the oral immunotherapy composition; and removing the single dose package comprising the selected amount of the oral immunotherapy composition from the identified dosage container.

According to some embodiments, a method of retrieving a single dose package comprising a selected dosage of an oral immunotherapy composition includes removing the single dose package comprising the selected amount of the oral immunotherapy composition from an identified dosage container, wherein the identified dosage container is identified using a dosage identifier on the dosage container that is associated with the selected dosage, and wherein the dosage container is identified from a plurality of different dosage containers comprising different dosage identifiers associated with different dosages of the oral immunotherapy composition.

According to some embodiments, a method of dispensing a selected dosage of an oral immunotherapy composition to a patient includes removing the single dose package comprising the selected amount of the oral immunotherapy composition from an identified dosage container, wherein the identified dosage container is identified using a dosage identifier on the dosage container that is associated with the selected dosage, and wherein the dosage container is identified from a plurality of different dosage containers comprising different dosage identifiers associated with different dosages of the oral immunotherapy composition; and dispensing the selected dosage of the oral immunotherapy composition to the patient.

According to some embodiments, a method of treating an allergy in a patient, includes identifying a dosage container associated with a selected dosage of an oral immunotherapy composition using a dosage identifier on the dosage container, wherein the dosage container is identified from a plurality of different dosage containers comprising different dosage identifiers associated with different dosages of the oral immunotherapy composition; removing a single dose package comprising the selected amount of the oral immunotherapy composition from the identified dosage container; and administering the selected dosage of the oral immunotherapy composition to the patient.

According to some embodiments, a method of treating an allergy in a patient includes removing a single dose package comprising a selected amount of the oral immunotherapy composition from an identified dosage container, wherein the identified dosage container is identified using a dosage identifier on the dosage container that is associated with the selected dosage, and wherein the dosage container is identified from a plurality of different dosage containers comprising different dosage identifiers associated with different dosages of the oral immunotherapy composition; and administering the selected dosage of the oral immunotherapy composition to the patient.

In any of the above embodiments, the allergy may be a food allergy.

In any of the above embodiments, the plurality of dosage containers may be contained within a housing.

In any of the above embodiments, the oral immunotherapy composition may include a peanut, tree nut, egg, dairy, or shellfish composition.

Any of the above methods may be performed using any of the above systems.

In any of the above embodiments, the method may be performed in a medical clinic.

In any of the above embodiments, the method may further include restocking the identified dosage container with single dose packages comprising an oral immunotherapy composition in the same amount as the removed single dose package.

In any of the above embodiments, the method may include replacing the identified dosage container with a new dosage container comprising the same dosage identification characteristic, wherein the new dosage container comprises a plurality of single dose packages.

In any of the above embodiments, the dosage identifier may include a color code, a shade code, or a number code associated with the selected dosage, and wherein identifying the dosage container comprises identifying the dosage container having the color code, the shade code, or the number code associated with the selected dosage.

In any of the above embodiments, identifying the dosage container may include using a dosage container position guide comprising the dosage identifier.

In any of the above embodiments, the method may further include selecting the dosage of oral immunotherapy for the patient.

In any of the above embodiments, the dosage of oral immunotherapy may be selected using a dosage identifier on a dosage folio previously provided to the patient.

In any of the above embodiments, the dosage of oral immunotherapy may be selected based on a tolerability of a previously administered dose by the patient.

In any of the above embodiments, the method may include dispensing a series of escalating dose units comprising the oral immunotherapy composition.

In any of the above embodiments, the method may include administering the series of escalating dose units to the patient.

In any of the above embodiments, the method may include monitoring the patient for a period of time for a reactive symptom following ingestion of a first escalating dose unit prior to dispensing or administering a second escalating dose unit.

In any of the above embodiments, the method may include monitoring the patient for a period of time for a reactive symptom following ingestion of each escalating dose unit.

In any of the above embodiments, the dosage of oral immunotherapy may be selected based on a dosage of the escalating dose unit ingested prior to detection of a reactive symptom.

In any of the above embodiments, the method may include dispensing a dosage folio to the patient for daily self-administration, wherein the dosage folio comprises a plurality of daily dose units comprising the selected dosage of the oral immunotherapy composition.

In any of the above embodiments, the method may include monitoring the patient for a period of time for a reactive symptom following dispensing or administering the selected dosage of the oral immunotherapy composition to the patient.

In any of the above embodiments, the patient may be a human.

In any of the above embodiments, administering the selected dosage may include mixing the oral immunotherapy composition with food.

In any of the above embodiments, one or more capsules or tablets containing the oral immunotherapy composition may be opened prior to mixing the oral immunotherapy composition with food.

BRIEF DESCRIPTION OF THE DRAWINGS

FIGS. 7A-7E are side views of a dosage folio illustrating various steps in transitioning the dosage folio from a closed configuration (FIG. 7A) to a fully open configuration (FIG. 7E) in accordance with an embodiment of the present technology.

DETAILED DESCRIPTION

Figure 1:
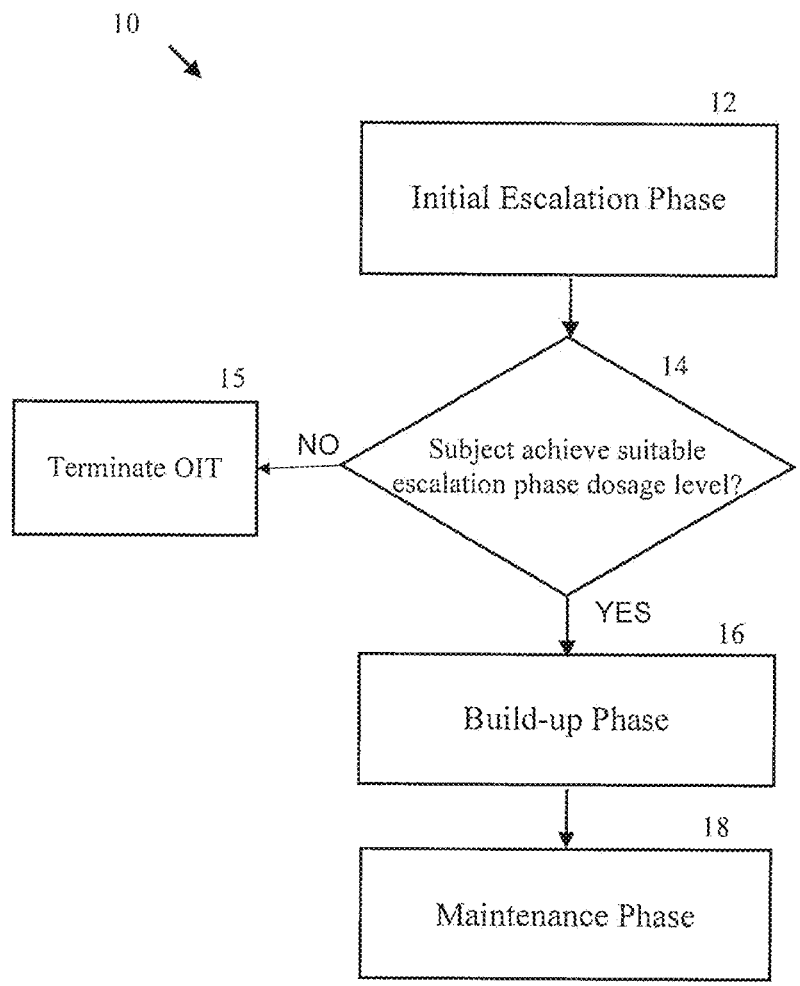
FIG. 1 is a block diagram illustrating a method of conducting an oral immunotherapy regimen on a subject in need thereof in accordance with an embodiment of the present technology.

Oral immunotherapy dosing regimens are both complex and highly tailored to an individual patient response over time. Generally, such regimens involve starting the patient at very low allergen dosage levels and increasing the allergen dosage slowly over time. During therapy, if a patient is not tolerating a dosage level well, the attending physician may either decrease the dosage or keep it level over a period of time before again increasing the dosage level. Thus, the oral immunotherapy dosing regimen is based largely on individual response, and can be highly variable. Furthermore, precise dosing of the oral immunotherapy drug in people with serious food allergy is not only important for efficacy, but critical for patient safety. In view of dosing complexity and the possibility, as well as the seriousness, of dosing errors, measures are needed to mitigate the risk of errors.

The system described herein facilitates dispensing of oral immunotherapy doses by providing a convenient platform for organizing and identifying dosages. The system includes (a) a plurality of dosage containers and (b) a housing having an internal cavity that retains the plurality of dosage containers. Each dosage container contains a plurality of detached single dose packages comprising an identical dosage of an oral immunotherapy composition. Additionally, the single dose packages in different dosage containers have different dosages of the oral immunotherapy composition. To aid the user in identifying the correct dosage of the oral immunotherapy composition, each dosage container comprises a dosage identification characteristic that associates the dosage container with the dosage of oral immunotherapy composition contained by the single dose packages contained by the dosage container.

A user (such as a doctor, nurse, or other clinician) can identify a dosage container corresponding to a selected dosage of the oral immunotherapy by using the dosage identification characteristic present on the dosage container. As further described herein, it is important that the correct dosage is dispensed to the patient to avoid dangerous adverse reactions. The user can remove a single dose package from the identified dosage container. If desired, the user can verify that the single dose package is correct by comparing the dosage identification characteristic present on the single dose package to the dosage identification characteristic present on the dosage container.

I. Definitions

As used herein, the singular forms "a," "an," and "the" include the plural reference unless the context clearly dictates otherwise.

The term "dosage identification characteristic" refers to any amount, number, letter, symbol, color, shading or other characteristic that is uniquely associated with a dosage of an oral immunotherapy composition.

The term "dosage level" describes any dosage identification characteristic other than a measured amount of the oral immunotherapy or an active ingredient in the oral immunotherapy composition that is associated with a particular dosage of an oral immunotherapy composition.

The term "subject" and "patient" are interchangeably used herein to describe a mammal, such as a human, with an allergy to a substance.

It is understood that aspects and variations of the invention described herein include "consisting" and/or "consisting essentially of" aspects and variations.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, stages, or characteristics may be combined in any suitable manner in one or more examples of the technology. The headings provided herein are for convenience only and are not intended to limit or interpret the scope or meaning of the technology. For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

II. Oral Immunotherapy Treatment Regimens

Many OIT regimens include a series of dose administration phases: initial day escalation, interval escalation dosing, and maintenance. Other phases and/or patient-specific tailoring of the regimen are also contemplated.

Initial day escalation typically occurs in a clinical setting and OIT dose administration and medical condition/symptom monitoring is facilitated by an attending physician or medical staff (e.g., nurse, physician's assistant, other permitted medical personnel, etc.). Dose escalation can begin on day 1 with administering a first dose (e.g., a lowest dose level of a composition comprising the offending antigen). Subsequently, the patient is monitored for reactive symptoms while being administered graduated doses at predetermined time intervals (e.g., 10 minutes, 20 minutes, 30 minutes, 45 minutes, 60 minutes, etc.) up to a maximum initial day dosage level (if tolerated). Accordingly, at the end of the initial day escalation phase, the subject either will have tolerated the maximum initial day dosage level (e.g., without exhibiting disqualifying symptoms), the subject will have tolerated a sub-maximum or intermediate dosage level (e.g., prior to exhibiting disqualifying symptoms). The specific dosage level achieved by the subject at the termination of the initial day escalation phase is accepted as the "desensitization" dose for further escalation.

The interval escalation dosing phase or build-up phase can occur primarily in the subject's home with intermittent treatment in the clinical setting. The build-up phase is designed to continually increase the desensitization dose of a particular subject over weeks and months to a maximum desensitization dose of an oral immunotherapy composition. Dosage level increases can occur in predetermined intervals (e.g., every 2 weeks) in the clinical setting (e.g., under observation), while the newly achieved up-dose level is maintained on a daily basis at home by the patient during the intervening interval period (e.g., 2 weeks). In a particular example, a subject having completed the initial dose escalation phase and having achieved a maximum initial day dosage level (e.g., the subject's desensitization dose), can be provided enough daily dosages to facilitate daily administration of the subject's desensitization dose every day for day 2 through day 14 of a two week interval period. The subject can then be administered the next dosage level in the clinical setting to begin a subsequent up-dosing interval. Ideally, the build-up phase continues until the subject achieves a desired daily desensitization dose (e.g., a dose sufficient to withstand an oral food challenge).

Following the build-up phase of an OIT regimen, the subject proceeds to a maintenance phase in which the subject continues to take the maximum achieved daily dose at home to maintain the achieved level of allergen desensitization.

FIG. 1 is a block diagram illustrating one embodiment of an OIT regimen 10 for desensitizing a subject to an offending allergen in accordance with an aspect of the present technology. Referring to block 12, the OIT regimen 10 includes an initial escalation phase in which a subject is administered a series of dosage levels within a clinical setting. The initial escalation phase 12 can be used to determine an initial desensitization dosage level for the subject or to determine if the OIT regimen is suitable for the patient. The OIT regimen 10 proceeds to decision block 14 where it is determined if the subject achieved a suitable escalation phase dosage level. For example, a medical professional can determine if a subject was able to tolerate a predetermined dosage level without experiencing deleterious symptoms (e.g., moderate or severe allergic reaction symptoms). If the subject did not tolerate the predetermined dosage level, the OIT regimen 10 is terminated (block 15). If, however, the subject did successfully tolerate the predetermined dosage level, the OIT regimen 10 continues to the build-up phase (block 16). During the build-up phase, the OIT regimen 10 can include a series of up-dosing intervals or cycles where subjects are administered increasingly higher dosage levels on predetermined intervals (e.g., every two weeks), while maintaining the new dosage level with daily doses self-administered at home. For example, after completing a dose cycle, a patient can return to the clinical setting to receive a higher dose than that just completed. The clinical professional can select, for example, the next higher dose and administer the dose to the patient in the clinical setting. If the patient tolerates the higher dose, then the patient may be provided with a folio or other package containing a cycle's worth (e.g., two weeks) of the dose level. In some embodiments, a subject may not tolerate the new daily dosage level (e.g., experience allergic reaction symptoms in the clinic and/or at home) and daily dosage levels can be altered accordingly (e.g., daily dosage levels can be lowered to previously tolerated dosage levels for a period of time before a further attempt at up-dosing).

The OIT regimen 10 further includes a maintenance phase (block 18). During the maintenance phase, the patient is administered a maintenance dose at home to maintain the achieved level of desensitization of the offending allergen in the subject. The maintenance dose may be a predetermined dose or may be a patient-specific dose, such as a maximum tolerated dose. One of ordinary skill in the art of immunotherapy, including OIT, will recognize other OIT regimens that may be conducted using various aspects of the present technology.

Throughout an OIT regimen, it is important to ensure that the correct dosage of allergen is administered to the subject, both in the clinical setting as well as outside of the clinical setting, for example for self-administered dosages. Any error in administration of the proper dosage level to a subject during the course of an OIT regimen can have dangerous and even life-threatening results.

III. Oral Immunotherapy Unit Dose Dispensing Systems

Provided herein are oral immunotherapy (OIT) unit dose dispensing systems that are useful for reducing medical/clinical staff dosing errors in the clinic or doctor's office, patient errors outside the doctor's office, and increasing overall patient compliance in oral immunotherapy regimens. Specific details of several embodiments of the technology are described below with reference to FIGS. 2-11. Although many of the embodiments are described below with respect to devices, systems, and methods for oral immunotherapy and delivery of therapeutic agents to patients for the treatment of peanut and other food allergy, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 2-11.

Figure 2:
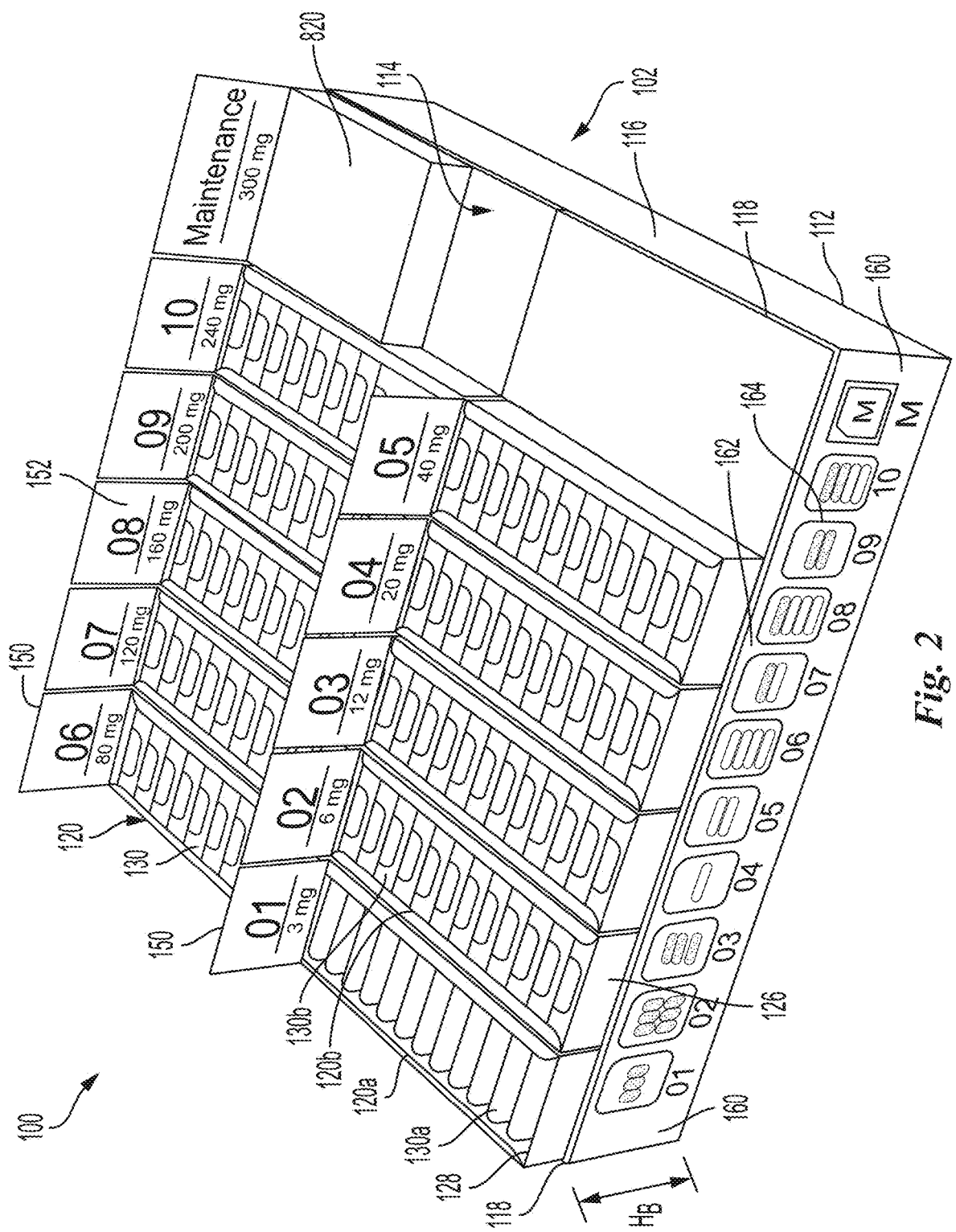
FIG. 2 is a front perspective view of a unit dose dispensing system configured in accordance with an embodiment of the present technology.

FIG. 2 is a front perspective view of a unit dose dispensing system 100 configured in accordance with an embodiment of the present technology. The system 100, for example, may be used to store, organize, identify and/or select a proper dosage for a specific patient during OIT administration. In one embodiment, the system 100 provides an accurate and consistent containment structure that reduces a likelihood of error when administering a unit dose to an OIT patient during treatment. For example, the system 100 includes a plurality of features to prevent administration of an incorrect and/or harmful dose of an offending allergen OIT composition to a patient. The illustrated unit dose dispensing system 100 includes a housing 102 having a base portion 112 with an internal cavity 114 that retains a plurality of dosage containers 120a and 120b. Each dosage container holds a plurality of single dose packages 130a and 130b. The single dose packages 130a and 130b each contain a single dose of a composition, such as the oral immunotherapy composition. The single dose packages within a given dosage container contain identical dosages. For example, dosage container 120a contains a plurality of single dose packages 130a with each single dose package 130a providing a first dose level (e.g., 3 mg), and dosage container 120b contains a plurality of single dose packages 130b with each single dose package 130b providing a second dose level (e.g., 6 mg), wherein the first dose level and the second dose level are different. Further, the single dose packages are detached from one another. Therefore, a user may retrieve a detached single dose package from a dosage container without needing to detach the single dose package from any other single dose package. During normal use, the unit dose dispensing system 100 comprising the housing 102, dosage containers 120 and single dose packages 130 are maintained at a physician's office or medical clinic, and facilitates efficiency and dosage accuracy during in-office patient OIT treatment, including, but not limited to, the build-up phase portion of OIT during which up-dosing of a patient occurs.

The housing 102 may accommodate any number of dosage containers 120, including at least 2 different dosage containers, at least 3 different dosage containers, at least 4 different dosage containers, at least 5 different dosage containers, at least 6 different dosage containers, at least 10 different dosage containers, at least 20 different dosage containers, at least 50 different dosage containers, or at least 100 different dosage containers. Generally, the housing 102 may accommodate between 3 and about 100 different dosage containers.

The housing 102 may include the base portion 112 to provide an open containment system in which the internal cavity 114 is exposed and/or accessible such that a single dose package 130 providing a single dose with a predetermined dosage (e.g., 3 mg, 6 mg, 12 mg, 20 mg, 40 mg, 80 mg, 120 mg, 160 mg, 200 mg, 240 mg, 300 mg, etc.) of oral immunotherapy composition retained therein may be accessible at any time. In another embodiment, the housing 102 may include a lid portion (not shown) that can be sized to releasably cover the base portion 112, thereby providing closed containment of system components retained within the internal cavity 114. For example, a lid portion (not shown) may be utilized during packaging and shipping and/or for storage of the system 100 when not in use.

In some embodiments, the dosage containers 120a and 120b are detached containers, which can be individually removed from the housing 102 of the system. If the number of single dose packages within a dosage container is low or the dosage container is empty, the dosage container can be removed from the system and replaced with a dosage container containing additional single dose packages. In some embodiments, the dosage containers 120 are configured to be refilled with single dose packages 130.

As described further herein, the system 100 may include a number of features for accurately identifying and selecting a proper OIT dose for a specific patient prior to administration. For example, the system 100 may incorporate dosage identification characteristics including, but not limited to, color coding and/or variation (e.g., graduated shading, etc.), numeric coding, symbols, capsule orientation and configuration within single dose packages 130a, etc. In additional embodiments, various aspects of the shape (e.g., rounded corners, 90° angled corners) and/or orientation of the dosage containers (e.g., 120a) carrying varying dosage levels within the housing 102 may be used to further uniquely characterize specific OIT dosage levels. Further embodiments may include unique sound signals when single dose packages are dispensed (e.g., removed) from a respective dosage containers. One of ordinary skill in the art will recognize that other sensory (e.g., visual, touch, audible, etc.) features can be used to uniquely characterize specific dosage levels within the system 100.

In some embodiments, the housing 102 may be a reusable box, constructed of cardboard, paperboard, plastic, metal, or other suitable material, and configured to hold the plurality of dosage containers, preferably of varying dosage levels (e.g., a first dosage level, second dosage level, third dosage level, etc.). In certain embodiments, the housing 102 is configured to hold one or more dosage containers of each dosage level of an OIT regimen. The internal cavity 114 of the housing 102 provided by the base portion is configured to allow physical and/or visual access to the dosage containers held within. In further embodiments, the internal cavity 114 is configured to contain the dosage containers 120 in one, two, three or more rows such that all dosage containers 120 are physically and/or visually accessible within the base portion 112 when the housing 102 is in an open configuration (e.g., no lid portion enclosing the internal cavity 114).

In various embodiments, the dosage containers 120a and 120b may be reusable, recyclable or disposable and, in some embodiments, can be constructed of cardboard, paperboard, plastic, metal or other suitable material. Further, the dosage containers 120a and 120b are configured to hold single dose packages 130a and 130b. In some embodiments, the dosage containers each hold between 1 and 50 single dose packages therein. In certain embodiments, the dosage containers can each hold 5, 6, 7, 8, 9, 10, 12, 15 or 20 single dose packages therein.

Figure 3A:
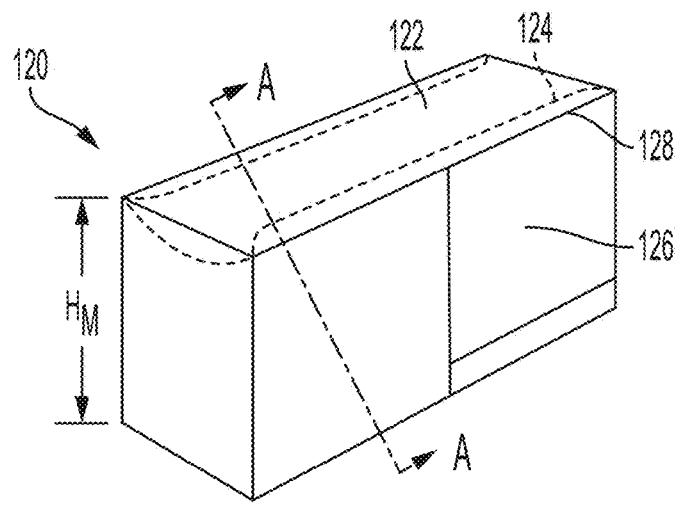
FIG. 3A is a front perspective view of a dosage container in a closed configuration in accordance with an embodiment of the present technology.
Figure 3B:
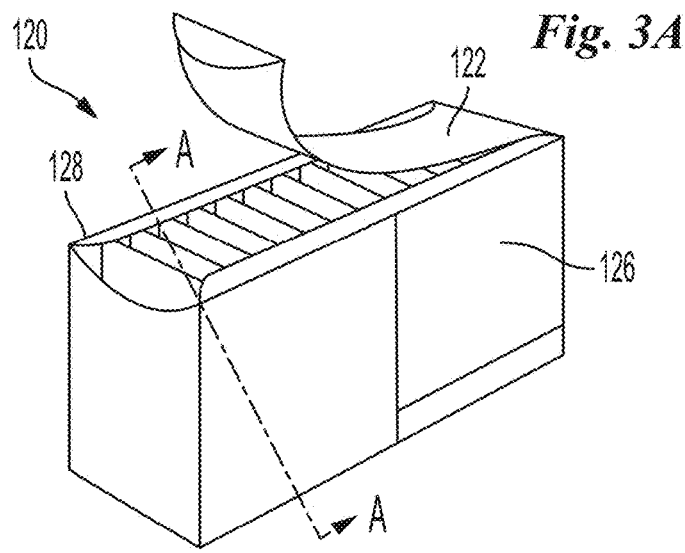
FIG. 3B is a front perspective view of the dosage container of FIG. 3A in an open configuration in accordance with an embodiment of the present technology.

FIGS. 3A and 3B are front perspective views of a dosage container 120 in closed (FIG. 3A) and open (FIG. 3B) configurations, respectively, in accordance with an embodiment of the present technology. The dosage containers 120 can include a removable top portion 122, which may be opened to provide access to the contents of the dosage containers 120 (e.g., the plurality of detached single dose packages contained therein). In some embodiments, the removable top portion 122 is delineated by perforated lines 124 in the dosage container 120 (FIG. 3A). In other embodiments, however, the top portion 122 may not be removable and the top portion can be opened and closed repeatedly as needed to retrieve or store the detached single dose packages 130 therein. Referring to FIGS. 2, 3A, and 3B together, the dosage container 120 is configured to hold a plurality of detached single dose packages 130 in an organized manner until dispensed, such as in an upright or stacked configuration. The detached single dose packages 130 are accessible when the top portion 122 is removed and/or the dosage container 120 is in the open configuration (FIG. 3B).

Referring again to FIGS. 2, 3A, and 3B together, the housing 102 includes the base portion 112 having a lower outer surface (not shown) and a plurality of base side walls 116 having a base height $H_B$. In some embodiments, the base height $H_B$ (FIG. 2) can be less than a height $H_M$ of dosage container side walls 126 (FIGS. 3A-3B). In these embodiments, the dosage containers 120 can be positioned within the internal cavity 114 of the housing 102 such that an upper edge 128 of the dosage containers 120 are positioned above an upper edge 118 of the base side walls 116. In this embodiment, portions of the module side walls 126 can include dose level identification information that is readily visible above the side walls 116 of the housing 102 (FIG. 2). In another embodiment, not shown, the upper edge 128 of the dosage containers 120 can be relatively flush with an upper edge 118 of the base side walls 116. In this embodiment, the housing 102 can be stackable with other materials, additional system modules and/or other system components. In other embodiments, the height $H_B$ can be greater than the height $H_M$.

In some embodiments, the single dose packages 130 are non-reusable containers designed to hold a quantity of oral immunotherapy composition intended for administration as a single dose, and preferably to be used promptly after the detached single dose package 130 is opened. The detached single dose package 130 may comprise, among other options, blister pack, a foil packs, or a sachet. The oral immunotherapy composition dose contained within the detached single dose package 130 may be in the form of one or more capsules, tablets, or powder. In certain embodiments the detached single dose package 130 is a blister pack on which a designation of dosages, instructions and/or warnings is printed on the bister back. In some embodiments, the blister pack can contain capsules or tablets encased between two materials such as aluminum foil and polyvinyl chloride film such that the capsule(s) or tablet(s) can be pressed through the aluminum foil backing. In some embodiments, the blister pack can have peel-push backing and can be designed with child-resistant features. Oral immunotherapy composition doses can be administered in any suitable way. For example, capsules or tablets may be swallowed whole or caplets may be opened and the contents mixed with food or drink. In some embodiments, a single dose package 130 is a sachet and the oral immunotherapy composition is emptied from the opened sachet into food or drink.

The oral immunotherapy composition can comprise one or more food protein allergens from a particular food source or sources. For example, the formulation may include peanut allergens, tree nut allergens, dairy allergens, egg allergens, seed allergens, soybean, wheat, shellfish and fish allergens, among other known food allergens. Such allergen formulations may be manufactured in a manner that delivers consistent/repeatable proportions of the critical individual allergens such that protein content can be highly controlled. In a particular example, the single dose package 130 may contain a dosage level including, but not limited to, about 0.5 mg to about 100 mg, such as about 0.5 mg, 1 mg, 1.5 mg, 2 mg, 3 mg, 5 mg, 6 mg, 10 mg, 12 mg, 15 mg, 20 mg, 40 mg, 50 mg, 80 mg, 100 mg, 120 mg, 150 mg, 160 mg, 200 mg, 240 mg, 250 mg, 300 mg, 400 mg, 500 mg, 600 mg, 700 mg, 800 mg, 900 mg, or 1000 mg. The dosage amount of the oral immunotherapy composition refers to the amount of protein from a food associated with the food allergy to be treated. In certain embodiments, the dosage level in an individual single dose package 130 can be provided in a single capsule or tablet, or in more than one capsule or tablet.

Figures 4A, 4B, 4C, 4D:
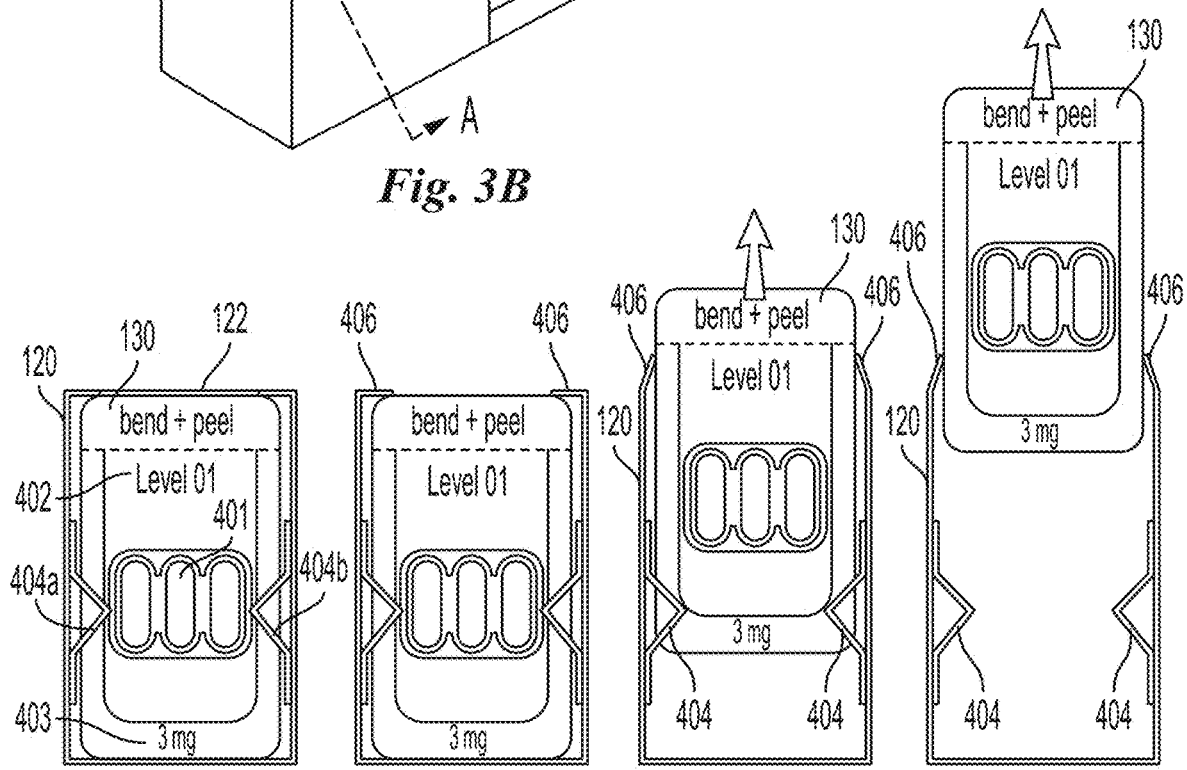
FIG. 4A is a cross-sectional view of the dosage container of FIG. 3A along line A-A in accordance with an embodiment of the present technology.
FIG. 4B is a cross-sectional view of the dosage container of FIG. 3B along line A-A in accordance with an embodiment of the present technology.
FIGS. 4C and 4D illustrate various steps in the dispensing of the single dose package of FIGS. 4A-4B from the dosage container in accordance with an embodiment of the present technology.

FIG. 4A is a cross-sectional view of an exemplary dosage container 120 of FIG. 3A along line A-A illustrating a single dose package 130 held within the dosage container 120 in accordance with an embodiment of the present technology. In the illustrated embodiment, the single dose package 130 contains one or more capsules 401 comprising OIT composition in a dosage amount according to the level indicated on the single dose package 130 via one or more identification characteristics (e.g., dosage level number 402, measurement of dosage level 403, etc.). In some embodiments, the single dose package contains one or more capsules comprising an oral immunotherapy composition in a dosage amount according to an amount indicated on the single dose package. In the embodiment shown in FIG. 4A, the dosage container 120 comprises an organizing feature such as a plurality of spaced apart side supports 404a and 404b between which the lateral edges of single dose package 130 can be secured in a substantially vertical orientation and in a row (e.g., one behind another). As shown in FIG. 4A, a pair of side supports 404a, 404b maintain the single dose package 130 in an upright position and spaced apart from adjacent single dose packages 130 (see, e.g., FIG. 3B) to facilitate storage, dispensing and tracking of single dose packages 130.

FIG. 4B is a cross-sectional view of the dosage container 120 of FIG. 3B along line A-A illustrating the single dose package 130 held within the dosage container 120 following removal of the top portion 122 (see, e.g., FIG. 4A). FIGS. 4C and 4D illustrate various steps in the dispensing of the single dose package 130 of FIGS. 4A-4B from the dosage container 120 in accordance with an embodiment of the present technology. In the illustrated example, remaining upper tabs 406 can fold upward allowing the single dose package 130 to be removed from the dosage container 120. In some embodiments, additional single dose packages (not shown) having the same dosage level can be inserted in the dosage containers 120 between adjacent spaced apart side supports 404 for the purposes of restocking the dosage container 120 for further use in the clinical setting, or the entire dosage container 120 can be replaced with a new dosage container containing single dose packages of the same dose.

Referring back to FIG. 2, and in one embodiment, the unit dose dispensing system housing 102 holds a plurality of dosage containers 120 providing a system 100 that includes single dose packages having a spectrum of dosage levels consistent with a specific OIT regimen. In a particular example, a peanut OIT regimen may require a system 100 comprising single dose modules that provide a 3 mg dose, a 6 mg dose, a 12 mg dose, a 20 mg dose, a 40 mg dose, an 80 mg dose, a 120 mg dose, a 160 mg dose, a 200 mg dose, a 240 mg dose and a 300 mg dose. In a specific embodiment, the dose dispensing system housing 102 holds a dosage container 120 for a 40 mg dosage level, wherein said dosage container 120 contains 12 single dose packages 130 (e.g., blister packs), wherein each single dose package 130 has a single 40 mg dose, and wherein the single 40 mg dose is provided in two capsules.

As discussed above, the system 100 includes a plurality of dosage identification characteristics for facilitating accurate and safe selection of a proper OIT dose for a patient prior to administration. In some embodiments, the dosage containers 120 and/or the single dose packages 130 in a system can be color-coded or shade-coded, with each single dose package 130 having a different color (e.g., red, orange, yellow, green, blue, etc.) or different shading density than the other single dose packages 130 depending on the dosage level (e.g., dosage levels 1-10 and Maintenance dosage level in FIG. 2) to facilitate visual differentiation in dosage level, and, in some embodiments, to permit quick restocking of dosage container 120. In some embodiments, color coding or shading can be graduated by dosage level. For example, color changes from one level to the next (in sequential order) can include logical graduation of color shade within a particular color (e.g., light color to dark color). In other embodiments, color changes from one level to the next may correspond to other color schemes (e.g., order on color wheels, order of visual spectrum of colors, etc.). In further embodiments, changes from one level to the next may correspond with color meaning associations. For example, the highest dosage levels may be color coded in shades of oranges and reds (e.g., indicating caution and warning), while the lowest dosage levels may be color coded in shades of greens and blues (e.g., indicating safety and stability). In still further embodiments, color changes can include a combination of graduated changes of color shade and color changes. In some embodiments, dosage containers have a color associated with an immunotherapy type and shading-coding can be used to indicate dosage levels.

In certain embodiments, the single dose packages 130 comprise capsule blister packs and the dosage container 120 is labeled with an illustration showing a unique capsule configuration for each dosage level to further prevent dosage container box restocking errors. In addition to color coding and providing unique capsule configurations for each of the available dosage levels within the system 100, other dosage identification characteristics can be used in addition to or instead of color coding and capsule configuration. For example, dosage identification characteristics may also include numeric coding (e.g., level numbering 01, 02, 03, etc.), measurement of dosage level (e.g., 3 mg, 6 mg, 12, mg, etc.), and/or other unique identifying symbols. In further embodiments, unique audible signals can be generated when removing individual single dose packages 130 from a dosage container 120 to further assist a medical practitioner or attendant in confirming that the dosage level dispensed is accurate for the particular patient.

In some embodiments, capsules or tablets may be color coded or sized according to an amount of oral immunotherapy composition. For example, 1 mg capsules or tablets may be colored or sized differently than 2 mg capsules or tablets. Single dose packages 130 may include several different sized and/or colored capsules or tablets. For example, a 3 mg single dose package may include one 1 mg red capsule and one 2 mg blue capsule, and a 6 mg single dose package of the same system may include three 2 mg blue capsules.

In further reference to FIG. 2, the housing 102 may be configured to retain the dosage containers 120 within the internal cavity 114 in a modular pattern designed to facilitate a medical practitioner to quickly identify a proper dosage level. For example, dosage containers may be positioned within the housing in ascending order of dosage level, or in another embodiment, descending order of dosage level. As further shown in FIG. 2, the unit dose dispensing system 100 may also be provided with one or more insertable dosage container position guides 150. A dosage container position guide 150 can provide easily visible information regarding the location of any individual dosage container 120 within the housing. For example, the dosage container position guide 150 may be oriented vertically with respect to the lower outer surface (not shown) and extend vertically beyond the height $H_M$ of the dosage containers 120 (FIG. 3A) to provide a label region 152. In some embodiments, the dosage container position guide is printed on the removable top portion of the dosage container, and the removable top portion can be folded to display the dosage container position guide.

The label region 152 of the dosage container position guide 150 can include single dosage module identification, which may include corresponding dosage identification characteristics (e.g., color-coding, numeric coding, units of measurement, symbols, etc.) to further facilitate retrieval of single dosage package 130 from the proper dosage container 120. Accordingly, in many embodiments, the dosage container position guide 150 can provide a guide for initial placement of each dosage container 120 within the internal cavity 114 of the housing 102 as well as provide a guide for retrieval and/or restocking of individual single dose packages 130 in a manner that reduces error.

In various embodiments, the dosage container position guide 150 can be a reusable, removable card that is manually inserted into the housing 102 in a vertical orientation. In other embodiments, the dosage container position guide 150 may be permanently or non-permanently attached to the adjacent module side walls 126 (see, e.g., FIG. 3A) via adhesive, clips, slots or other retaining feature.

In addition to the dosage container position guide(s) 150, the housing 102 may provide additional dosage level and other identification information. Referring back to FIG. 2, the housing 102, for example, may include a label region 160, such as a region on a side wall 116 of the housing 102. In one some embodiments, the label region 160 can provide product and/or company information 162. Additional information may also be included such as product reorder information and the like. The label region 160 may further include other information with regard to dosage level identification, such as in a visible single dosage configuration guide 164. In the illustrated embodiment, the single dosage configuration guide 164 provides illustrated identification of the orientation, size and color/texture of each capsule contained within each dosage level. Such dosage level characteristics and cross-check with the single dosage configuration guide 164 can ensure additional risk reduction in administering a patient an improper OIT dosage during use.

In some embodiments, the label region 160 can be printed directly on a side wall 116 of the housing 102. In other embodiments, the label region 160 with information 162 and guide(s) 164 can be separately attached such as one or more labels adhered to the side walls 116 via adhesive or the like.

In some embodiments, the system 100 may provide additional dosage dispensing modules and containers for facilitating administration of proper OIT dosages during the build-up phase as well as other phases (e.g., initial escalation phase, maintenance phase, etc.). For example, FIGS. 5A-5C, 6A-6B, and 7A-7E illustrate a plurality of views of dosage folios 500 for patient use outside the clinical setting. In a particular embodiment, a dosage folio 500 can be used to self-administer a daily dose at home during intervening intervals between up-dosing in the clinical setting during the build-up phase.

Figure 5A:
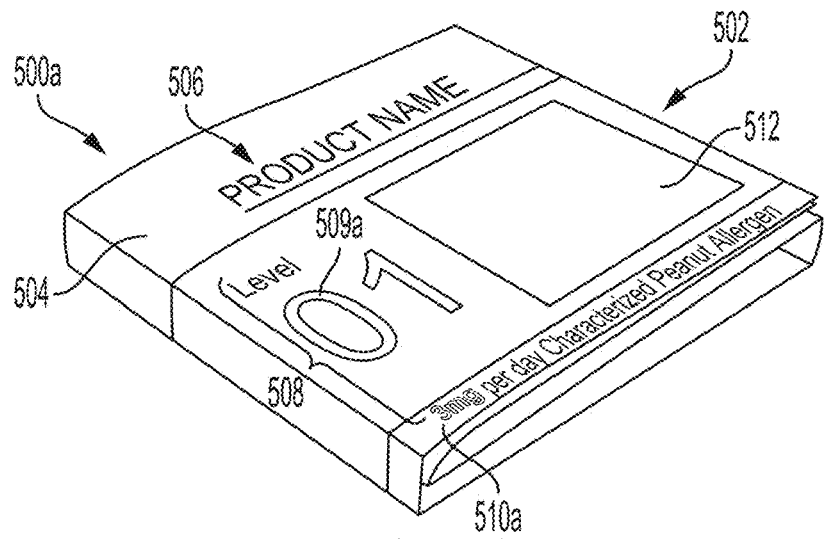
FIGS. 5A, 5B, and 5C are front perspective views of dosage folios for patient use outside the clinical setting in accordance with an embodiment of the present technology.
Figure 5B:
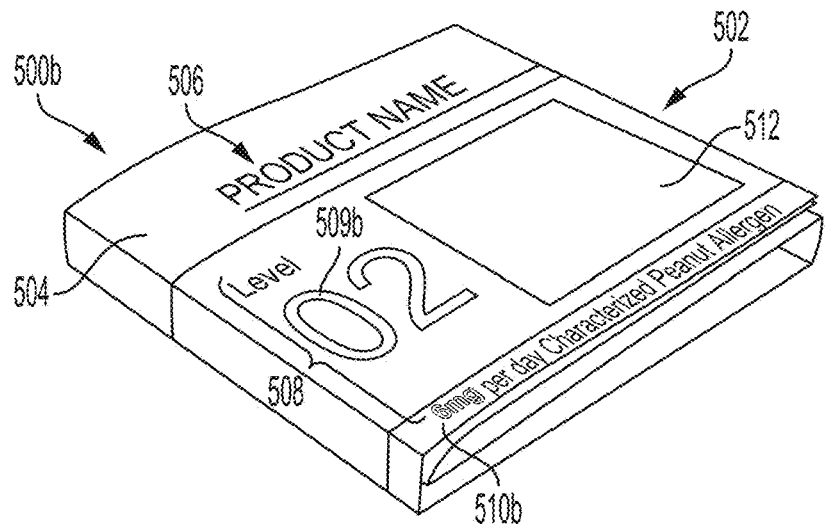
Figure 5C:
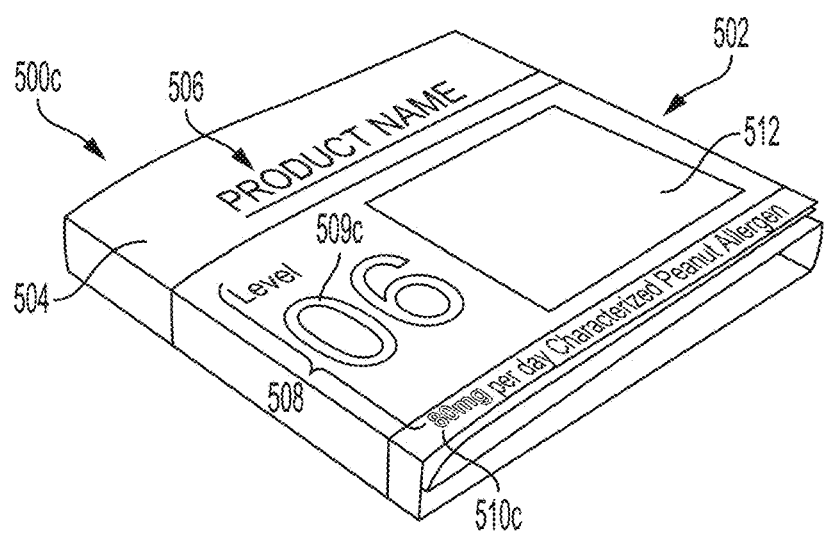

FIGS. 5A-5C are front perspective views of dosage folios 500a, 500b, 500c (generally referred to as "500"), respectively, for patient use outside the clinical setting in accordance with an embodiment of the present technology. In reference to FIGS. 5A-5C together, single dose folios 500 can be folded packets providing identifying information 502, dosage capsules (not shown) and other instructions and daily note-taking portions (not shown). As illustrated in FIGS. 5A-5C, a front portion 504 of the folio 500 can include identifying information 502 that includes, but is not limited to, product and/or company information 506, dosage level identification 508 (e.g., numeric coding 509, measurement of dosage level 510, unique dosage level color coding (not shown), etc.), and space 512 for pharmacy prescription label and/or patient identification. The folios 500a, 500b and 500c can be identified as containing daily self-administrable doses having different dosage levels. For example, folio 500a is identified by numeric code 509a and measurement of dosage level 510a, and folio 500b is identified by numeric code 509b and measurement of dosage level 510b. Other readily visible differences may include unique color coding (not shown). In various embodiments, the unique dosage level identification characteristics present on the front portion 504 of the folio 500 can correspond to the unique dosage level identification characteristics present on the dosage containers 120 and single dose packages 130 illustrated in FIGS. 2-4D.

Figure 6A:
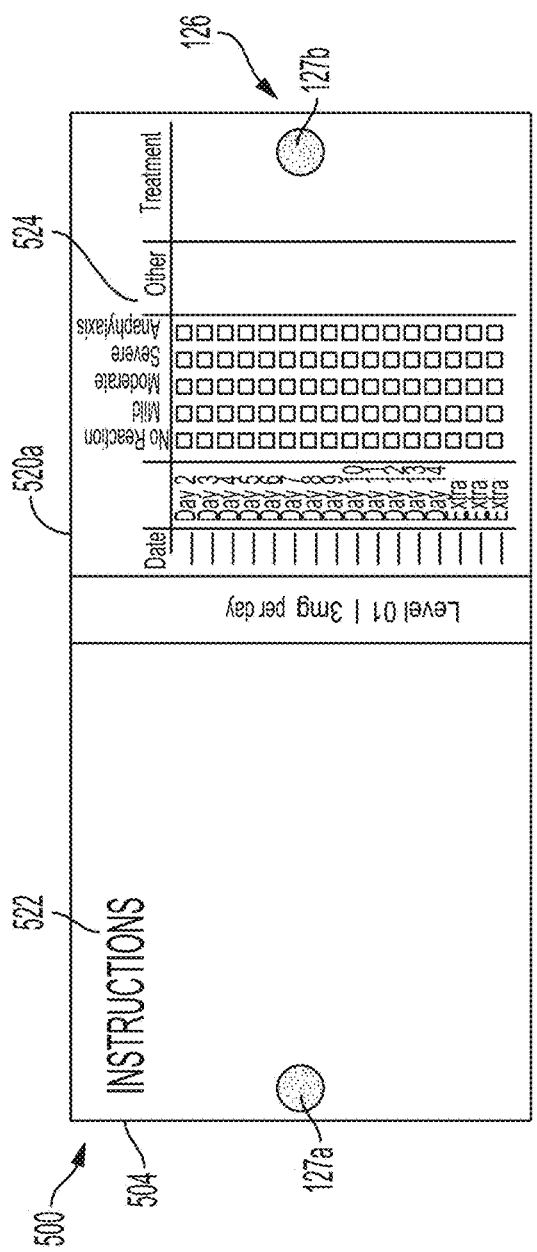
FIG. 6A is a top view of a dosage folio in a partially open configuration in accordance with an embodiment of the present technology.

FIG. 6A is a top view of a dosage folio 500 in a partially open configuration in accordance with an embodiment of the present technology. As illustrated, the dosage folio 500 can be partially opened by rotating the front portion 504 to reveal an internal portion 520a and exposing folio surfaces supplying information, such as instructions for use 522 and patient log 524 to record information pertaining to self-administration of OIT dosages and reactions following such administration. For example, the log 524 can allow for patient-reporting of an onset of systemic symptoms (e.g., no reaction, mild, moderate, severe, anaphylaxis). In a particular example, the patient can record if he/she experienced symptoms such as flushing, intensive itching on the skin, sneezing, runny nose, sense of heat, gastro-intestinal discomfort, headache, agitation/anxiety, etc., as well as report what treatment for the symptoms were used, if any. In some embodiments, the dosage folio 500 can be retained and/or released from the closed configuration (FIGS. 5A-5C) to the partially open configuration (FIG. 6A) by a restraining feature 126 (e.g., mating hook 127a and loop tabs 127b, clasp, adhesive, etc.).

Figure 6B:
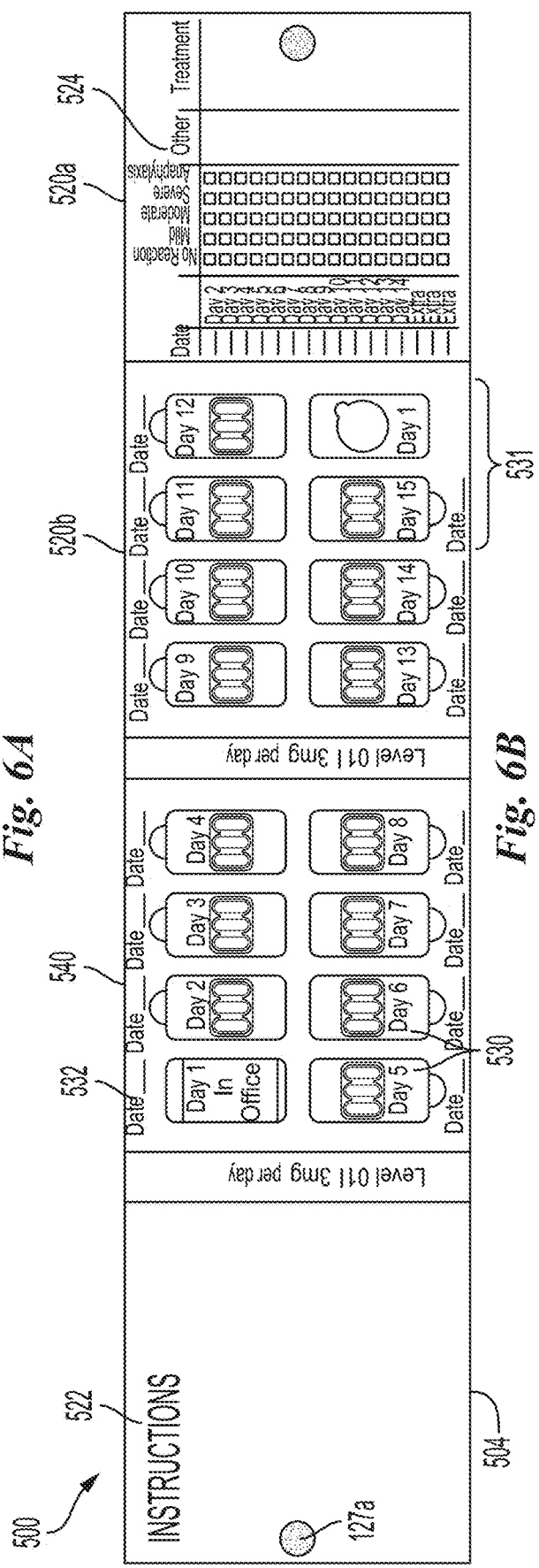
FIG. 6B is a top view of the dosage folio of FIG. 6A in a fully-open configuration in accordance with an embodiment of the present technology.

FIG. 6B is a top view of the dosage folio 500 of FIG. 6A in a fully-open configuration in accordance with an embodiment of the present technology. As illustrated, the dosage folio 500 can be fully opened to provide access to daily dosage units 530 retained therein. According to some embodiments, each daily dosage unit 530 can comprise a plurality of capsules or tablets and each daily dosage unit can be independently openable such that each daily dosage can be accessed without accessing the other daily dosages. FIGS. 7A-7E are side views of a single dose folio illustrating various steps in transitioning the dosage folio 500 from a closed configuration (FIG. 7A) to a fully open configuration (FIG. 7E) in accordance with an embodiment of the present technology. For example, FIG. 7B illustrates an intermediate step in opening the dosage folio 500 from the closed configuration (FIG. 7A) to a partial open configuration (e.g., FIG. 6A) by rotating the front portion 504 away from internal portions 520a and 520b. As shown in FIGS. 7C-7E, a user can horizontally separate the front portion 504 from internal portion 520a exposing internal portion 520b comprising a plurality of daily dosage units 530 and back portion 540 comprising a plurality of daily dosage units 530. When in use, the dosage folio can be folded and unfolded as illustrated in steps depicted in FIGS. 7A-7E for access and storage of daily dosage units.

Referring back to FIG. 6B, daily dosage units 530 are accessible to the patient when the dosage folio is in the fully open configuration. In the illustrated example, the OIT regimen sets forth patient self-administration of the tolerated daily dose outside the clinic setting between day 2 and day 14 of a two-week interval between up-dosing of the patient during the build-up phase. In other embodiments, the intervening interval can be longer or shorter and the dosage folio 500 may include more or fewer daily dosage units 530 to accommodate a specific OIT regimen. For example, dosage folios may include about 7 to about 35 daily dose units, i.e., one week to five weeks' worth of daily doses. In some embodiments, folios include fifteen dosage units, which provides two weeks' worth of doses plus a couple of extra doses. As illustrated, in some embodiments, the daily dosage units 530 can be arranged in a grid-like pattern and a grid location associated with the first day may lack a daily dosage unit, since the dosage for the first day may have been administered at the doctor's office. The daily dosage units 530 provided in the dosage folio 500 can be identical. Further provided to track and record patient self-administration, the folio may comprise date recording lines 532 adjacent each daily dosage unit 530. The folio 500 may also include extra daily dosage units 531 to be used as instructed/needed.

A plurality of dosage folios 500 may be retained within a separate module (not shown) for storage and retrieval of such folios to prescribe to patients. Such modules may be included in the housing 102 or may be stored in a separate housing container (not shown) and/or as part of a kit for dispensing pharmaceutical products (e.g., relating to OIT regimens).

Figure 8A:
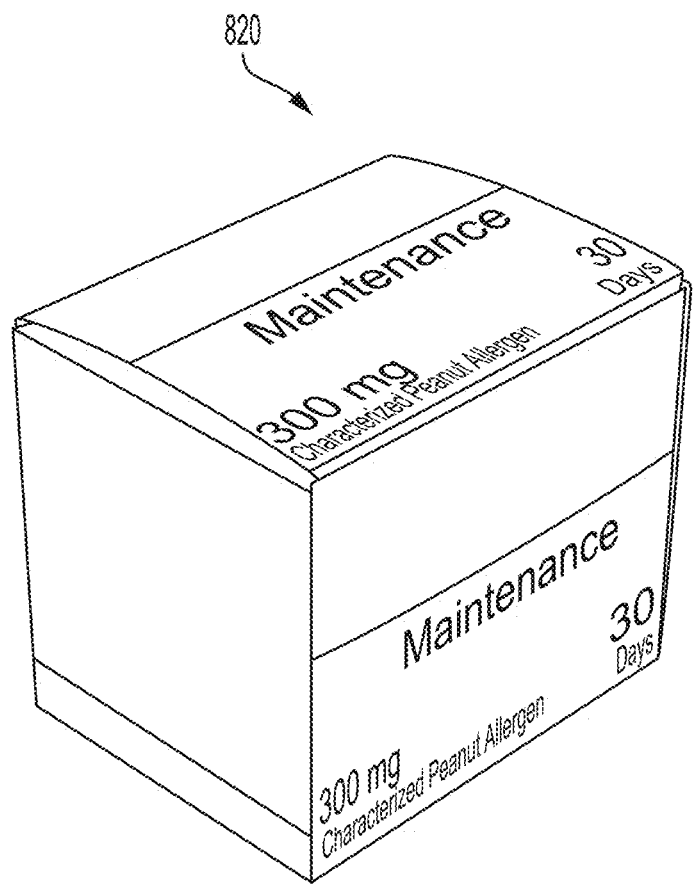
FIGS. 8A and 8B are front perspective views of a maintenance dosage container in a closed configuration and an open configuration, respectively, in accordance with embodiments of the present technology.
Figure 8B:
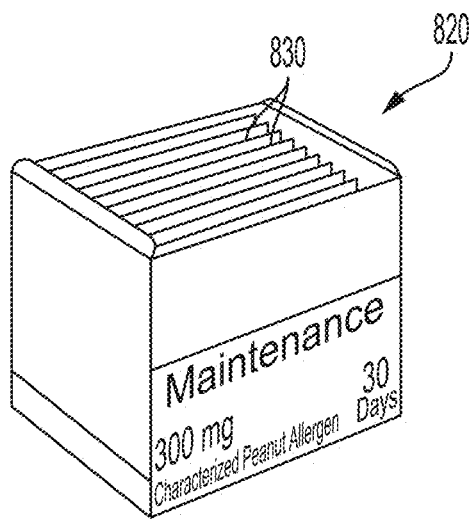

The system 100 may also include a module for organizing, storing and dispensing dosages for use during the maintenance phase of an OIT regimen. FIGS. 8A and 8B are front perspective views of a maintenance dosage container 820 in a closed configuration (FIG. 8A) and the maintenance dosage container 820 in an open configuration (FIG. 8B) in accordance with embodiments of the present technology.

Referring to FIGS. 8A and 8B together, the maintenance dosage container 820 can include a plurality of maintenance dosage folios or sachets 830 each containing maintenance dose to be self-administered daily to maintain allergen desensitization. The maintenance dose folios or sachets 830 can be organized (e.g., such as in an upright or stacked configuration) and/or retained in spaced-apart fashion as described above with respect to the dosage containers 120 (FIGS. 3A-4D).

In some embodiments, and as illustrated in FIG. 2, the maintenance dosage container 820 can be positioned within the system housing 102; however, in other embodiments, the maintenance dosage container 820 is a stand-alone dosage module within the system 100 and/or as a component of a kit for dispensing pharmaceutical products (e.g., relating to OIT regimens).

Figure 9:
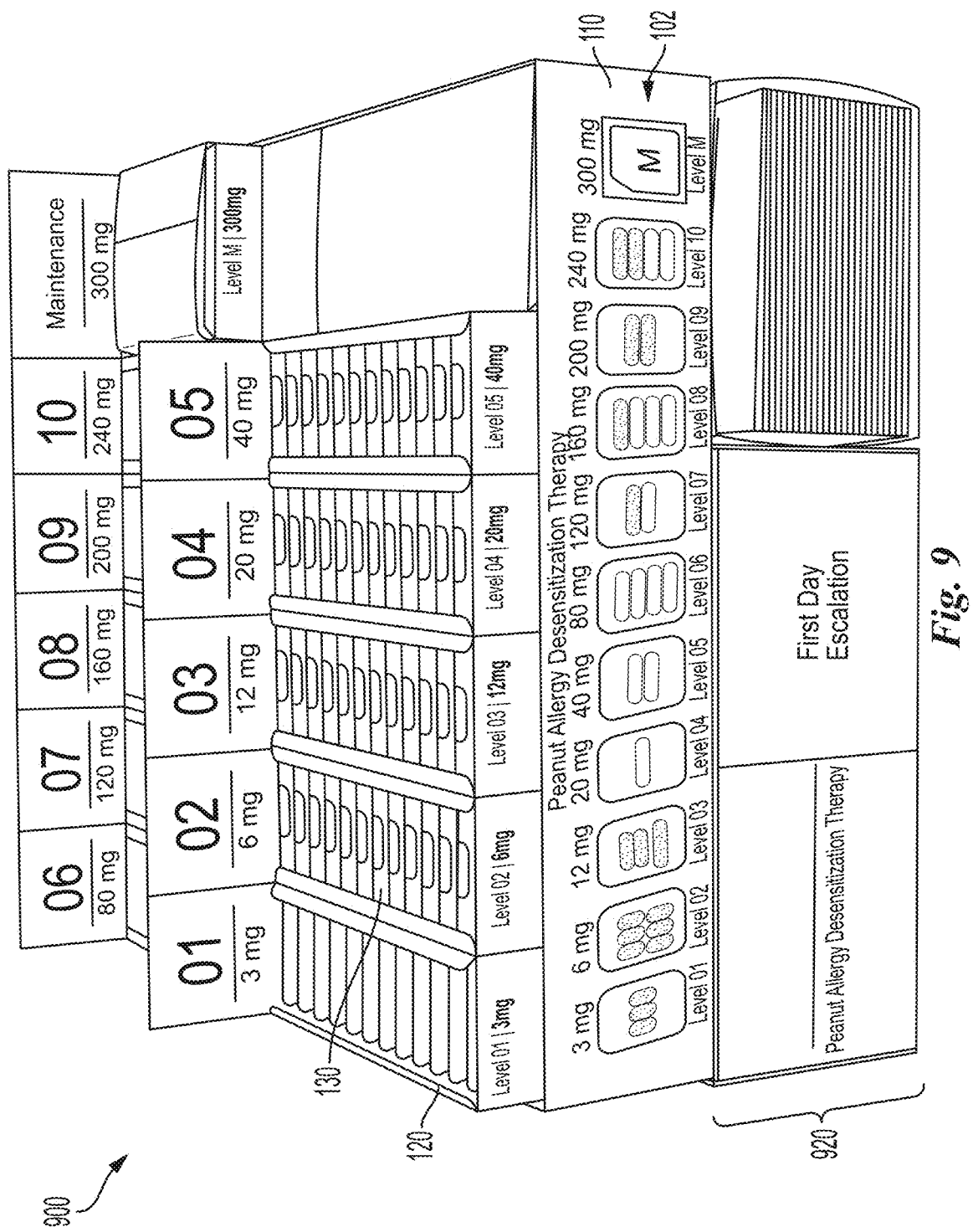
FIG. 9 is a front perspective view of a unit dose dispensing system in accordance with another embodiment of the present technology.

FIG. 9 is a front perspective view of a unit dose dispensing system 900 in accordance with another embodiment of the present technology. The unit dose dispensing system 900 includes many of the same features as the system 100 shown in FIG. 2. For example, the system 900 includes the housing 102 for organizing and retaining a plurality of single dosage containers 120 and single dose packages 130 in a manner that is safe and effective for administration of a variety of OIT dosage levels (e.g., during a build-up phase of an OIT regimen). However, the system 900 can also include a plurality of modules 920 suitable to administer a variety of OIT dosage programs for additional phases and aspects of an OIT regimen. For example, the system 900 can include modules 920 comprising dosage units for the initial escalation phase of an OIT regimen in a manner that is safe and effective for administration.

Figure 10B:
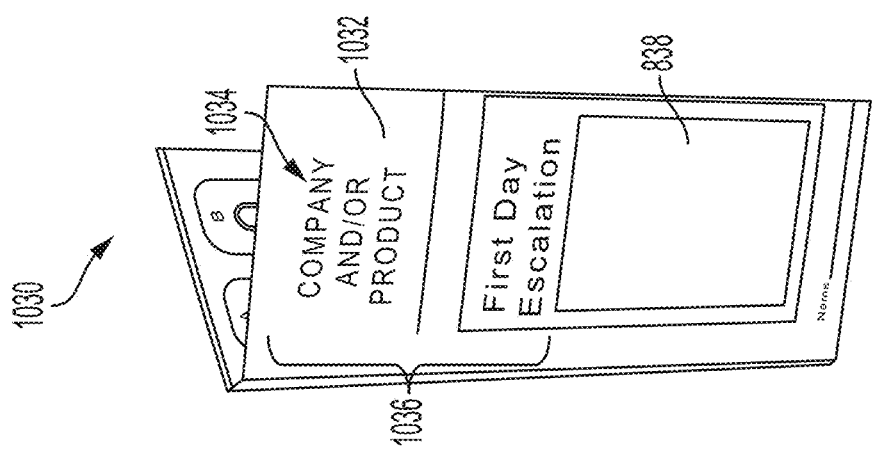
FIGS. 10A and 10B are front perspective views of an initial escalation dosage module and an initial escalation folio in accordance with embodiments of the present technology.
Figure 10A:
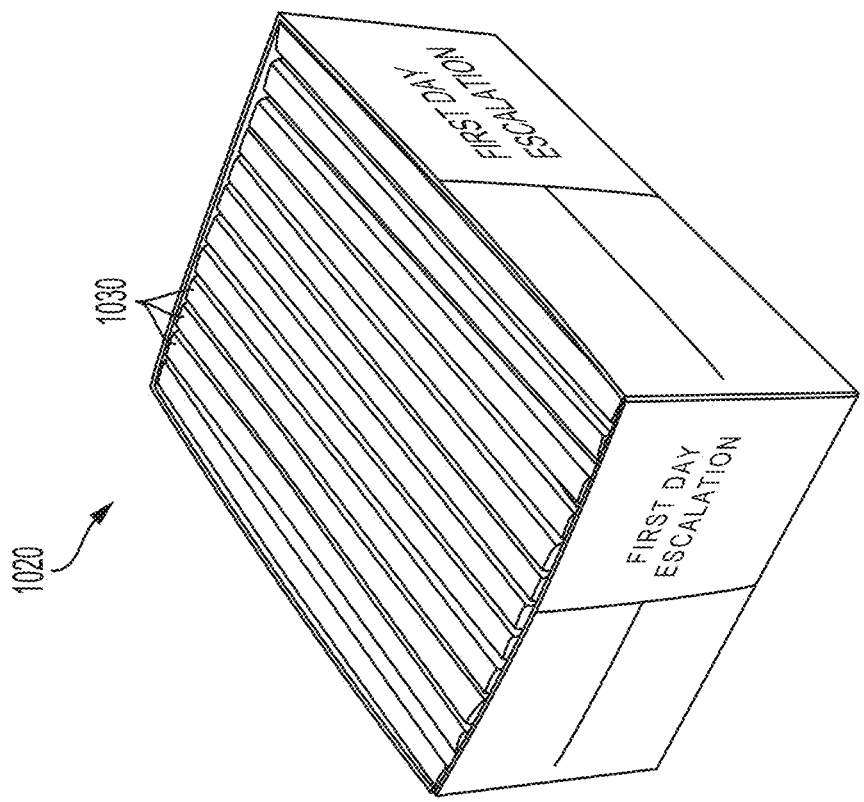

Referring to FIG. 9, the system 900 may include a container for organizing, storing and dispensing dosages for use during the initial escalation phase of an OIT regimen. FIGS. 10A and 10B are front perspective views of an initial escalation dosage module 1020 and an initial escalation folio 1030 in accordance with embodiments of the present technology. Referring to FIG. 10B, and in one embodiment, the initial escalation folio 1030 can be a single use (non-reusable) bi-fold folio made of cardstock or other material. A front portion 1032 of the initial escalation folio 1030 can include identifying information 1034 that includes, but is not limited to, product and/or company information 1036 and space 838 for pharmacy prescription label and/or patient identification. As shown in FIG. 10A, a plurality of initial escalation folios 1030 can be retained within the initial escalation dosage module 1020. In some embodiments, the initial escalation dosage module 1020 can be positioned within the system housing 102; however, in other embodiments, the initial escalation dosage module 1020 can be a stand-alone dosage module within the system 900 and/or as a component of a kit for dispensing pharmaceutical products (e.g., relating to OIT regimens).

Figure 10C:
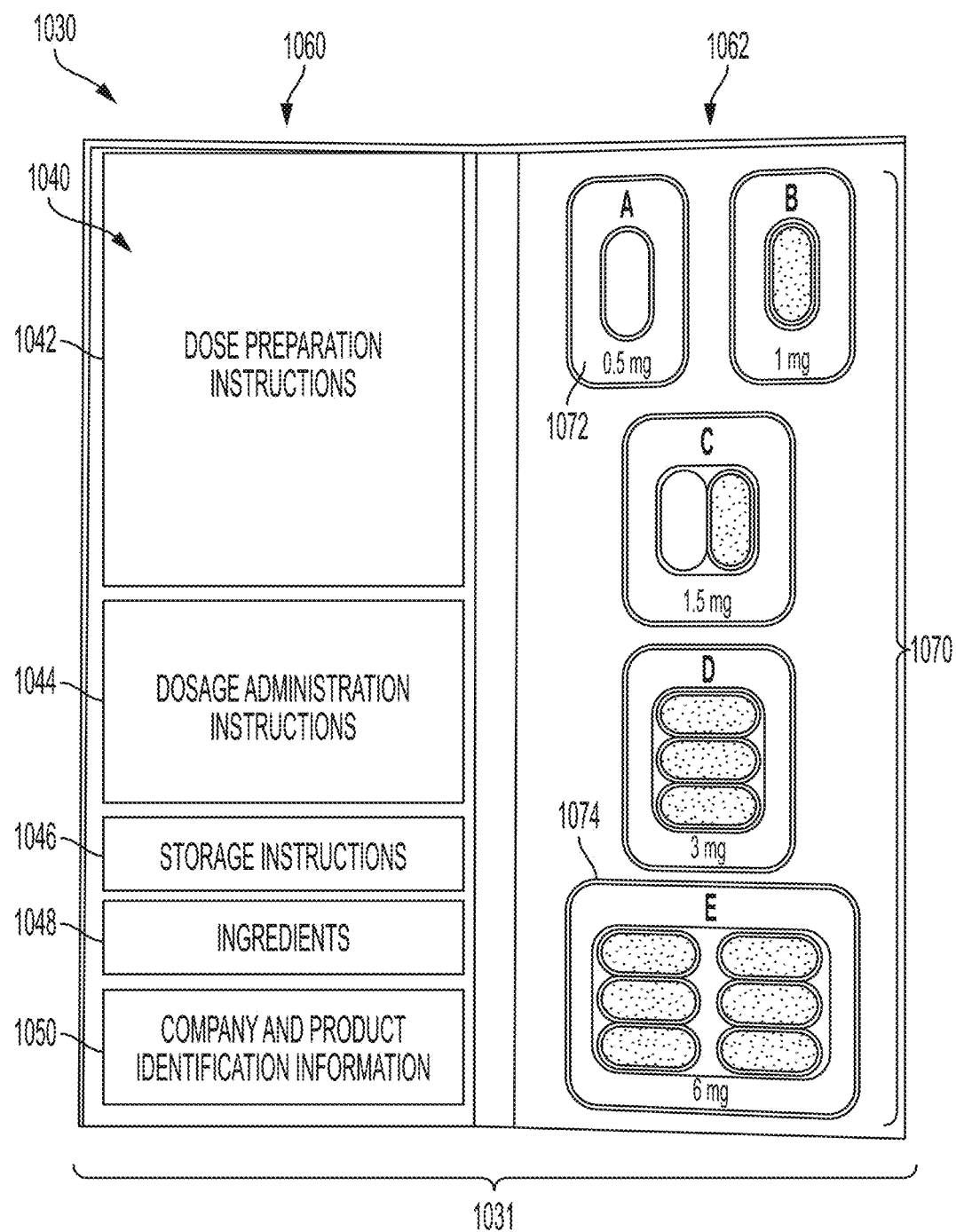
FIG. 10C is a front view of the initial escalation folio of FIG. 8B in an open configuration and in accordance with an embodiment of the present technology.

FIG. 10C is a front view of the initial escalation folio 1030 of FIG. 10B in an open configuration and in accordance with an embodiment of the present technology. As illustrated, and in the open configuration, the initial escalation folio 1030 comprises content information 1040 on a first side 1060 of an internal portion 1031 of the folio 1030. The content information 1040 may include, for example, dose preparation instructions 1042, dosage administration instructions 1044, storage instructions 1046, ingredients 1048 and company/product identification information 1050 among other information. A second side 1062 of the internal portion 1031 comprises a series of dose units 1070 from a first lowest dose 1072 to a maximum dose 1074 that are releasably retained within the folio material. For example, the dose units 1070 may be retained within individual foil packs attached to or integrated with the second side 1062 of the folio 1030. During an initial escalation phase, a patient can be prescribed an initial escalation folio 1030 wherein each of the dose units 1070 are administered to the patient within a clinical setting in pre-determined or physician-determined time intervals (e.g., according to an OIT regimen). For example, during the course of an initial escalation phase, the patient can be administered the first lowest dose 1074 up to the maximum dose 1074 as tolerated.

Figure 11:
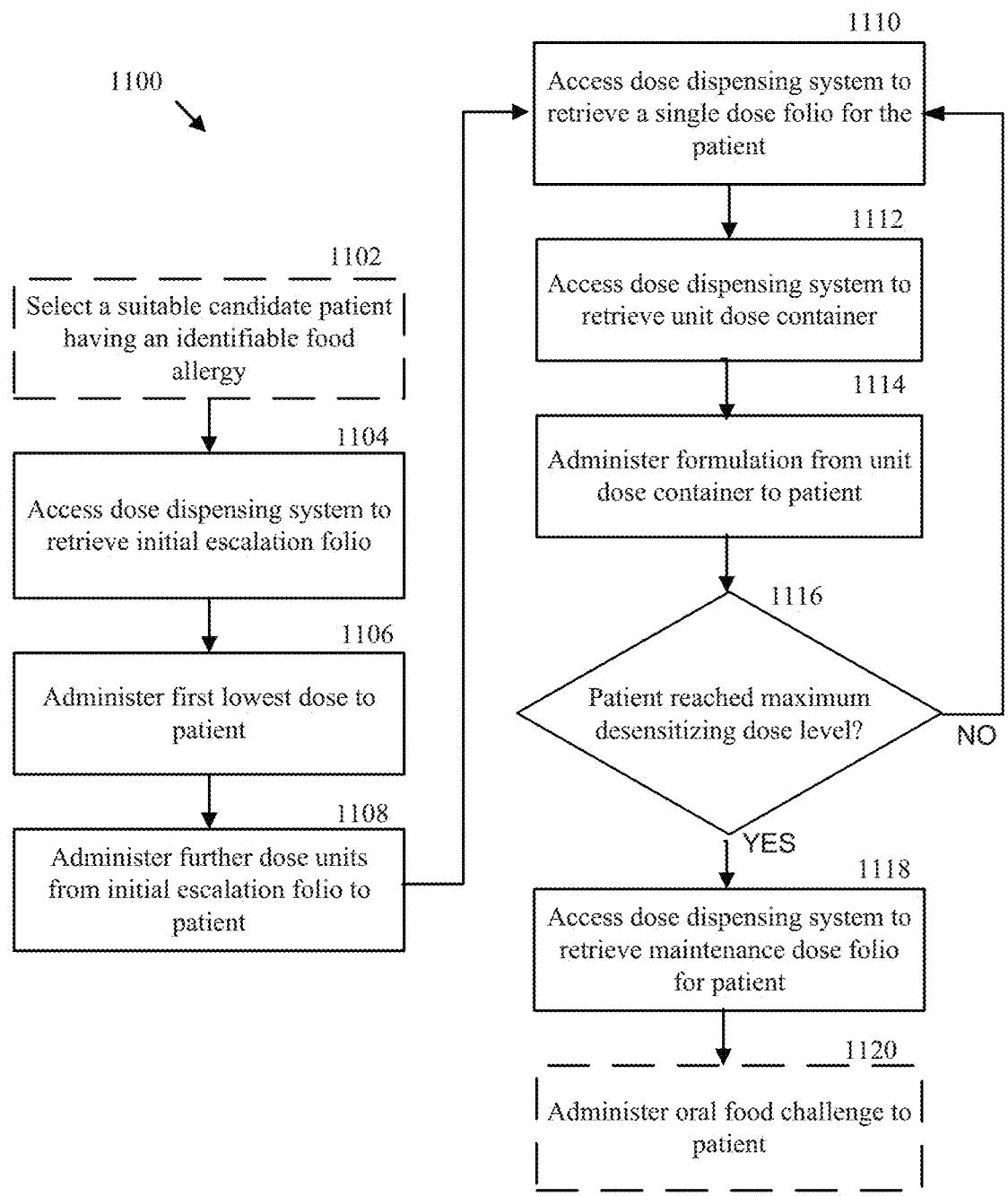
FIG. 11 is a block diagram illustrating a method of providing an oral immunotherapy regimen to a patient in a clinical setting in accordance with an aspect of the present technology.

IV. Selected Examples of Treatment Procedures for Providing an OIT Therapeutic Regimen Using Dose Dispensing Systems Disclosed herein are methods and treatment procedures for providing an OIT therapeutic regimen to a patient in a clinical setting using the dose dispensing system. In particular, FIG. 11 is a block diagram illustrating a method 1100 of providing an OIT regimen to a patient in a clinical setting in accordance with an aspect of the present technology. The method 1100 can optionally include selecting a suitable candidate patient having an identified food allergy for providing OIT (block 1102). For example, a suitable patient can include a patient having had one or more allergic reactions to the offending food allergen and for which was confirmed by conventional means (e.g., prick test, blood test, oral food challenge, etc.) by an attending physician.

The method 1100 can include accessing a dose dispensing system to retrieve an initial escalation folio 1030 from an initial escalation module 1020 (block 1104) and begin the initial escalation phase of an OIT regimen by administering the first lowest dose 1072 from the initial escalation folio 1030 to the patient (block 1106). The method 1100 can also include administering further dose units 1070 from the initial escalation folio 1030 to the patient (block 1108) in a sequential manner until the patient demonstrates tolerance of the maximum dose 1074 or demonstrates intolerance of one of the prior dose units 1070, whichever comes first. The method 1100 can further include accessing the dose dispensing system to retrieve a dosage folio to provide the patient for home administration of daily unit doses at the highest dosage level tolerated by the patient (e.g., a first dosage level) from the initial escalation folio 1030 (block 1110). For example, when accessing the dose dispensing system, a clinician may cross-check dosage identifying characteristics (e.g., color-coding, numeric code, dosage level measurement, etc.) present on the dosage folio to ensure that the dosage folio contains daily unit doses having the patient-specific dosage level.

Following a predetermined time interval wherein the patient self-administers daily unit doses at the first dosage level, the method 1100 includes accessing the dose dispensing system to retrieve a single dose package from a dosage container (block 1112) and administering the OIT formulation provided therein to the patient (block 1114). In some embodiments, the single dose packaging includes a second dosage level that is one level higher than the first dosage level (e.g., the dosage level previously tolerated by the patient). In other embodiments, the single dose container includes an oral immunotherapy composition at the first dosage level, or in other embodiments, at a reduced dosage level depending on the patient's toleration of the allergen-containing formulation. When accessing the dose dispensing system, the clinician can cross-check dosage identifying characteristics (e.g., color-coding, numeric code, dosage level measurement, dosage/capsule configuration and orientation, etc.) present on the dosage container as well as the single dose package to ensure that the single dose package contains a unit dose having the patient-specific dosage level.

In optional decision block 1116, an evaluation of the patient's current dose level is evaluated. In some embodiments, no evaluation of the patient's current dose level is evaluated, and the patient continues to receive the maintenance dosage. When the patient continues to a maintenance phase of the OIT regimen, the dose dispensing system is accessed to retrieve a maintenance dose folio from the maintenance dosage container to provide the patient for home administration of daily maintenance doses (block 1118). For example, when accessing the dose dispensing system, a clinician may cross-check dosage identifying characteristics (e.g., color-coding, numeric code, dosage level measurement, dosage/capsule configuration and orientation, etc.) present on the maintenance dosage container and/or the maintenance dose folio to ensure that the folio contains daily unit doses having the patient-specific maintenance dosage level. If in optional decision block 1116, it is determined that the patient has not reached his/her maximum desensitizing dose level, the patient can continue the build-up phase (e.g., continue increasing dosage levels for a patient) by going back to block 1110.

Optionally, the method 1100 may continue by administering the patient an oral food challenge (block 1120) to determine if the level of desensitization to the offending allergen was achieved via the OIT regimen.

The detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. For example, while various embodiments of the dose dispensing system is described for use for administration of pharmaceutical formulations pertaining to oral immunotherapy, one or ordinary skill in the art will recognize that the dose dispensing system described herein may also be used to dispense pharmaceutical formulations and other compounds associated with other forms of treatment and conditions. Where the context permits, singular or plural terms may also include the plural or singular term, respectively.

EXEMPLARY EMBODIMENTS

The following embodiments are exemplary and should not be considered to limit the claimed invention.

Embodiment 1

A system for administering an oral immunotherapy regimen to a patient, comprising:

a plurality of dosage containers comprising a plurality of detached single dose packages comprising the same dosage of an oral immunotherapy composition, wherein the single dose packages in different dosage containers comprise different dosages of the oral immunotherapy composition, and wherein the dosage containers comprises a dosage identifier that associates the dosage container with the dosage of oral immunotherapy composition contained by the single dose packages contained in the dosage container; and a housing having an internal cavity that retains the plurality of dosage containers.

Embodiment 2

The system of embodiment 1, wherein the single dose packages comprise the dosage identifier.

Embodiment 3

The system of embodiment 1 or 2, wherein the dosage identifier is a dosage level of the oral immunotherapy composition.

Embodiment 4

The system of any one of embodiments 1-3, wherein the dosage identifier comprises color-coding or shade-coding, and wherein each dosage is associated with a different color or shading.

Embodiment 5

The system of any one of embodiments 1-4, wherein the dosage identifier comprises numeric coding, and wherein the numeric coding indicates an order in which the dosage levels increase or decrease.

Embodiment 6

The system of any one of embodiments 1-5, wherein the dosage identifier comprises the dosage.

Embodiment 7

The system of any one of embodiments 1-6, wherein the oral immunotherapy composition is a powder.

Embodiment 8

The system of any one of embodiments 1-7, wherein the plurality of single dose packages comprise one or more capsules or tablets comprising the oral immunotherapy composition.

Embodiment 9

The system of embodiment 8, wherein the one or more capsules or tablets are visible without opening the single does package.

Embodiment 10

The system of embodiment 9, wherein the one or more capsules or tablets are arranged in a configuration associated with the dosage identifier for the dosage container.

Embodiment 11

The system of embodiment 10, wherein the system further comprises a dosage configuration guide that associates the configuration to the dosage identifier.

Embodiment 12

The system of any one of embodiments 1-11, wherein dosage containers comprise a plurality of supports spaced apart along a length of an inner wall of the dosage container, and wherein the dosage containers are configured to hold a single dose package in a substantially vertical orientation between the supports.

Embodiment 13

The system of any one of embodiments 1-12, further comprising an initial escalation module containing a plurality of initial escalation folios comprising a plurality of dose units in increasing dosage levels.

Embodiment 14

The system of any one of embodiments 1-13, further comprising a maintenance dosage container containing a plurality of maintenance dose units having the same dosage of the oral immunotherapy composition.

Embodiment 15

The system of any one of embodiments 1-14, wherein the dosage containers are configured to be refilled with single dose packages.

Embodiment 16

The system of any one of embodiments 1-14, wherein each dosage container is configured to be individually removed from the housing and replaced with a new dosage container.

Embodiment 17

The system of any one of embodiments 1-16, wherein the system comprises 3, 4, 5, or 6 or more different dosage containers.

Embodiment 18

The system of any one of embodiments 1-17, wherein the system comprises between 3 and about 100 different dosage containers.

Embodiment 19

The system of any one of embodiments 1-18, wherein the oral immunotherapy composition comprises a peanut, tree nut, egg, dairy, or shellfish composition.

Embodiment 20

The system of any one of embodiments 1-19, wherein the system further comprises an initial escalation folio comprising a series of escalating dose units comprising the oral immunotherapy composition.

Embodiment 21

The system of embodiment 20, wherein the series of dose units comprises at least one dose unit with a dosage of the oral immunotherapy composition that is lower than the lowest dosage of the single dose packages in any of the dosage containers.

Embodiment 22

The system of embodiment 20 or 21, wherein the escalating dose units are arranged in different configurations to identify different dosages.

Embodiment 23

The system of any one of embodiments 20-22, wherein the initial escalation folio is contained within the housing.

Embodiment 24

The system of embodiment 23, wherein the housing is configured to contain a plurality of initial escalation folios in a compartment of the housing.

Embodiment 25

The system of any one of embodiments 1-24, further comprising a dosage folio comprising:
a dosage identifier that associates the dosage folio to a dosage container within the plurality of dosage containers, and a plurality of daily dose units comprising the oral immunotherapy composition associated with the dosage identifier.

Embodiment 26

The system of embodiment 25, wherein the dosage folio comprises a patient log comprising a space identified for recording a date of administration of a daily dose unit.

Embodiment 27

The system of embodiment 25 or 26, wherein the dosage folio comprises a patient log comprising a space identified for recording a reactive symptom following ingestion of the daily dose unit.

Embodiment 28

The system of any one of embodiments 25-27, wherein the system comprises a plurality of dosage folios comprising different dosage identifiers, wherein the dosage folios comprise a plurality of daily dose units that correspond with the dosage identifier of the dosage folio.

Embodiment 29

A dosage folio comprising:
a plurality of daily dose units comprising an oral immunotherapy composition, wherein each daily dose unit is independently openable and comprises a plurality of capsules or tablets; and
a dosage identifier associated with the dosage of the daily dose units.

Embodiment 30

The dosage folio of embodiment 29, further comprising a patient log, wherein the patient log comprises a space identified for recording a date of administration of a daily dose unit.

Embodiment 31

The dosage folio of embodiment 30, wherein the patient log comprising a space identified for recording a reactive symptoms following ingestion of the daily dose unit.

Embodiment 32

The dosage folio of any one of embodiments 29-31, further comprising pictorial instructions for administering the oral immunotherapy composition.

Embodiment 33

The dosage folio of any one of embodiments 29-32, wherein the dosage identifier is a dosage level of the oral immunotherapy composition.

Embodiment 34

The dosage folio of any one of embodiments 29-33, wherein the dosage identifier comprises a color code or a shade code.

Embodiment 35

The dosage folio of any one of embodiments 29-34, wherein the dosage identifier comprises a numeric code.

Embodiment 36

The dosage folio of any one of embodiments 29-35, wherein the dosage identifier comprises the dosage of the daily dose units.

Embodiment 37

The dosage folio of any one of embodiments 29-36, wherein the oral immunotherapy composition is a powder.

Embodiment 38

The dosage folio of any one of embodiments 29-37, wherein the daily dose units are arranged in a grid pattern and a grid pattern location associated with a first day lacks a daily dose unit.

Embodiment 39

The dosage folio of embodiment 29-38, wherein the capsules or tablets are arranged in a configuration associated with the dosage identifier for the folio.

Embodiment 40

The dosage folio of any one of embodiments 29-39, wherein the oral immunotherapy composition comprises a peanut, tree nut, egg, dairy, or shellfish composition.

Embodiment 41

The dosage folio of any one of embodiments 29-40, wherein the dosage folio comprises about 7 to about 35 daily dose units.

Embodiment 42

A method of dispensing a selected dosage of an oral immunotherapy composition to a patient, comprising:
identifying a dosage container associated with a selected dosage of the oral immunotherapy composition using a dosage identifier on the dosage container, wherein the dosage container is identified from a plurality of different dosage containers comprising different dosage identifiers associated with different dosages of the oral immunotherapy composition;
removing a single dose package comprising the selected amount of the oral immunotherapy composition from the identified dosage container; and
dispensing the selected dosage of the oral immunotherapy composition to the patient.

Embodiment 43

A method of retrieving a single dose package comprising a selected dosage of an oral immunotherapy composition, comprising:
identifying a dosage container associated with the selected dosage of the oral immunotherapy composition using a dosage identifier on the dosage container, wherein the dosage container is identified from a plurality of different dosage containers comprising different dosage identifiers associated with different dosages of the oral immunotherapy composition; and removing the single dose package comprising the selected amount of the oral immunotherapy composition from the identified dosage container.

Embodiment 44

A method of retrieving a single dose package comprising a selected dosage of an oral immunotherapy composition, comprising:
removing the single dose package comprising the selected amount of the oral immunotherapy composition from an identified dosage container, wherein the identified dosage container is identified using a dosage identifier on the dosage container that is associated with the selected dosage, and wherein the dosage container is identified from a plurality of different dosage containers comprising different dosage identifiers associated with different dosages of the oral immunotherapy composition.

Embodiment 45

A method of dispensing a selected dosage of an oral immunotherapy composition to a patient, comprising:
removing the single dose package comprising the selected amount of the oral immunotherapy composition from an identified dosage container, wherein the identified dosage container is identified using a dosage identifier on the dosage container that is associated with the selected dosage, and wherein the dosage container is identified from a plurality of different dosage containers comprising different dosage identifiers associated with different dosages of the oral immunotherapy composition; and dispensing the selected dosage of the oral immunotherapy composition to the patient.

Embodiment 46

A method of treating an allergy in a patient, comprising:
identifying a dosage container associated with a selected dosage of an oral immunotherapy composition using a dosage identifier on the dosage container, wherein the dosage container is identified from a plurality of different dosage containers comprising different dosage identifiers associated with different dosages of the oral immunotherapy composition;
removing a single dose package comprising the selected amount of the oral immunotherapy composition from the identified dosage container; and
administering the selected dosage of the oral immunotherapy composition to the patient.

Embodiment 47

A method of treating an allergy in a patient, comprising:
removing a single dose package comprising a selected amount of the oral immunotherapy composition from an identified dosage container, wherein the identified dosage container is identified using a dosage identifier on the dosage container that is associated with the selected dosage, and wherein the dosage container is identified from a plurality of different dosage containers comprising different dosage identifiers associated with different dosages of the oral immunotherapy composition; and
administering the selected dosage of the oral immunotherapy composition to the patient.

Embodiment 48

The method of embodiment 46 or 47, wherein the allergy is a food allergy.

Embodiment 49

The method of any one of embodiments 42-48, wherein the plurality of dosage containers is contained within a housing.

Embodiment 50

The method of any one of embodiments 42-49, wherein the oral immunotherapy composition comprises a peanut, tree nut, egg, dairy, or shellfish composition.

Embodiment 51

The method of any one of embodiments 42-50, wherein the method is performed using the system of any one of embodiments 1-28.

Embodiment 52

The method of any one of embodiments 42-51, wherein the method is performed in a medical clinic.

Embodiment 53

The method of any one of embodiments 42-52, further comprising restocking the identified dosage container with single dose packages comprising an oral immunotherapy composition in the same amount as the removed single dose package.

Embodiment 54

The method of any one of embodiments 42-53, further comprising replacing the identified dosage container with a new dosage container comprising the same dosage identification characteristic, wherein the new dosage container comprises a plurality of single dose packages.

Embodiment 55

The method of any one of embodiments 42-54, wherein the dosage identifier comprises a color code, a shade code, or a number code associated with the selected dosage, and wherein identifying the dosage container comprises identifying the dosage container having the color code, the shade code, or the number code associated with the selected dosage.

Embodiment 56

The method of any one of embodiments 42-55, wherein identifying the dosage container comprises using a dosage container position guide comprising the dosage identifier.

Embodiment 57

The method of any one of embodiments 42-56, further comprising selecting the dosage of oral immunotherapy for the patient.

Embodiment 58

The method of embodiment 57, wherein the dosage of oral immunotherapy is selected using a dosage identifier on a dosage folio previously provided to the patient.

Embodiment 59

The method of embodiment 57 or 58, wherein the dosage of oral immunotherapy is selected based on a tolerability of a previously administered dose by the patient.

Embodiment 60

The method of any one of embodiments 42-59, further comprising dispensing a series of escalating dose units comprising the oral immunotherapy composition.

Embodiment 61

The method of embodiment 60, comprising administering the series of escalating dose units to the patient.

Embodiment 62

The method of embodiment 60 or 61, comprising monitoring the patient for a period of time for a reactive symptom following ingestion of a first escalating dose unit prior to dispensing or administering a second escalating dose unit.

Embodiment 63

The method of any one of embodiments 60-62, comprising monitoring the patient for a period of time for a reactive symptom following ingestion of each escalating dose unit.

Embodiment 64

The method of embodiment 62 or 63, wherein the dosage of oral immunotherapy is selected based on a dosage of the escalating dose unit ingested prior to detection of a reactive symptom.

Embodiment 65

The method of any one of embodiments 42-64, comprising dispensing a dosage folio to the patient for daily self-administration, wherein the dosage folio comprises a plurality of daily dose units comprising the selected dosage of the oral immunotherapy composition.

Embodiment 66

The method of any one of embodiments 42 and 45-64, further comprising monitoring the patient for a period of time for a reactive symptom following dispensing or administering the selected dosage of the oral immunotherapy composition to the patient.

Embodiment 67

The method of any one of embodiments 42-66, wherein the patient is a human.

Embodiment 68

The method of any one of embodiments 46-66, wherein administering the selected dosage comprises mixing the oral immunotherapy composition with food.

Embodiment 69

The method of embodiment 68, wherein one or more capsules or tablets containing the oral immunotherapy composition are opened prior to mixing the oral immunotherapy composition with food.

EXAMPLE

A subject suffering from a peanut allergy is selected for OIT treatment. During an initial escalation phase, a clinician retrieves an initial escalation folio from a peanut OIT dose dispensing system and the patient is administered escalating doses of 0.5 mg, 1.0 mg, 1.5 mg, 3 mg, and 6 mg in 30-minute intervals on day 1 of the treatment regimen. The patient is then provided a dosage folio containing a selected dose (e.g., 3.0 mg) on days 2-14 of the treatment regimen. Next, the patient is administered single doses of 6.0 mg, 12 mg, 20 mg, 40 mg, 80 mg, 120 mg, 160 mg, 200 mg, 240 mg, and 300 mg of peanut formulation from unit dose containers retrieved from single dosage modules contained within the peanut OIT dose dispensing system, and is provided corresponding dosage levels in single dose folios for self-administering daily unit doses in two-week intervals. The patient is then provided a maintenance dose folio containing a daily supply of 300 mg of peanut formulation to maintain peanut desensitization.

What is claimed is:

1. A system for administering an oral immunotherapy regimen to a patient, comprising:
   a plurality of dosage containers comprising a plurality of detached single dose packages comprising the same dosage of an oral immunotherapy composition,
   wherein the single dose packages in different dosage containers comprise different dosages of the oral immunotherapy composition,
   wherein the plurality of dosage containers are positioned within the system in ascending or descending order of dosage level, and
   wherein the dosage containers comprises a dosage identifier that associates the dosage container with the dosage of oral immunotherapy composition contained by the single dose packages contained in the dosage container;
   a housing having an internal cavity that retains the plurality of dosage containers; and
   an initial escalation folio comprising a series of escalating dose units comprising the oral immunotherapy composition.

2. The system of claim 1, wherein the single dose packages comprise the dosage identifier.

3. The system of claim 1, wherein the dosage identifier is a dosage level of the oral immunotherapy composition.

4. The system of claim 1, wherein the dosage identifier comprises color-coding or shade-coding, and wherein each dosage is associated with a different color or shading.

5. The system of claim 1, wherein the dosage identifier comprises numeric coding, and wherein the numeric coding indicates an order in which the dosage levels increase or decrease.

6. The system of claim 1, wherein the dosage identifier comprises the dosage.

7. The system of claim 1, wherein the oral immunotherapy composition is a powder.

8. The system of claim 1, wherein the plurality of single dose packages comprise one or more capsules or tablets comprising the oral immunotherapy composition.

9. The system of claim 8, wherein the one or more capsules or tablets are visible without opening the single does package.

10. The system of claim 9, wherein the one or more capsules or tablets are arranged in a configuration associated with the dosage identifier for the dosage container.

11. The system of claim 10, wherein the system further comprises a dosage configuration guide that associates the configuration to the dosage identifier.

12. The system of claim 1, wherein dosage containers comprise a plurality of supports spaced apart along a length of an inner wall of the dosage container, and wherein the dosage containers are configured to hold a single dose package in a substantially vertical orientation between the supports.

13. The system of claim 1, further comprising an initial escalation module containing a plurality of initial escalation folios comprising a plurality of dose units in increasing dosage levels.

14. The system of claim 1, further comprising a maintenance dosage container containing a plurality of maintenance dose units having the same dosage of the oral immunotherapy composition.

15. The system of claim 1, wherein the dosage containers are configured to be refilled with single dose packages.

16. The system of claim 1, wherein each dosage container is configured to be individually removed from the housing and replaced with a new dosage container.

17. The system of claim 1, wherein the system comprises 3 or more different dosage containers.

18. The system of claim 1, wherein the system comprises between 3 and about 100 different dosage containers.

19. The system of claim 1, wherein the oral immunotherapy composition comprises a peanut, tree nut, egg, dairy, or shellfish composition.

20. The system of claim 1, wherein the series of escalating dose units comprises at least one dose unit with a dosage of the oral immunotherapy composition that is lower than the lowest dosage of the single dose packages in any of the dosage containers.

21. The system of claim 1, wherein the escalating dose units are arranged in different configurations to identify dosages.

22. The system of claim 1, wherein the initial escalation folio is contained within the housing.

23. The system of claim 22, wherein the housing is configured to contain a plurality of initial escalation folios in a compartment of the housing.

24. The system of claim 1, further comprising a dosage folio comprising:
   a dosage identifier that associates the dosage folio to a dosage container within the plurality of dosage containers, and a plurality of daily dose units comprising the oral immunotherapy composition associated with the dosage identifier.

25. The system of claim 24, wherein the dosage folio comprises a patient log comprising a space identified for recording a date of administration of a daily dose unit.

26. The system of claim 24, wherein the dosage folio comprises a patient log comprising a space identified for recording a reactive symptom following ingestion of the daily dose unit.

27. The system of claim 24, wherein the system comprises a plurality of dosage folios comprising different dosage identifiers, wherein the dosage folios comprise a plurality of daily dose units that correspond with the dosage identifier of the dosage folio.

28. The system of claim 1, wherein the plurality of dosage containers are positioned within the system in ascending order of dosage level.

29. The system of claim 1, wherein the plurality of dosage containers are positioned within the system in descending order of dosage level.

* * * * *